(12) United States Patent
Browning et al.

(10) Patent No.: US 6,669,941 B1
(45) Date of Patent: *Dec. 30, 2003

(54) SOLUBLE LYMPHOTOXIN-β RECEPTOR AS A THERAPEUTIC AGENT FOR TREATING TH-1 CELL-ASSOCIATED AUTOIMMUNE DISEASE

(75) Inventors: Jeffrey L. Browning, Brookline, MA (US); Christopher D. Benjamin, Beverly, MA (US); Paula S. Hochman, Brookline, MA (US)

(73) Assignee: Biogen, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/303,262

(22) Filed: Apr. 30, 1999

Related U.S. Application Data

(63) Continuation of application No. 08/505,606, filed on Jul. 21, 1995, now Pat. No. 5,925,351.

(51) Int. Cl.$^7$ .................. A01N 38/00; A01N 38/16; A61K 39/00

(52) U.S. Cl. ................. 424/192.1; 424/192.1; 514/2; 514/8; 514/825; 514/885; 514/866; 514/903

(58) Field of Search ................. 514/2, 8, 825, 514/885, 866, 903; 424/143.1, 144.1, 145.1, 192.1

(56) References Cited

U.S. PATENT DOCUMENTS 4,959,457 A 9/1990 Bringman et al.

FOREIGN PATENT DOCUMENTS

WO 94/13808 6/1994

OTHER PUBLICATIONS

Amiri, Payman, et al., "Tumour necrosis factor ALPHA restores granulomas and induces parasite egglaying in schistosome–infected SCID mice," Nature 356:604–607 (1992).
Androlewicz, Matthew J., et al., "Lymphotoxin Is Expressed as a Heteromeric Complex with a Distinct 33–kDa Glycoprotein on the Surface of an Activated Human T Cell", J. Biol. Chem, 267:2542–47 (1992).
Browning, Jeffrey L., et al., "Lymphotoxin and an Associated 33–kDa Glycoprotein Are Expressed on the Surface of an Activated Human T Cell Hybridoma," J Immunology, 147: 1230–37 (1991).
Browning, Jeffrey L., et al. "Lymphotoxin Beta, a Novel Member of the TNF Family That Forms a Heteromeric Complex with Lymphotoxin on the Cell Surface," Cell 72: 847–56 (1993).
Browning, Jeffrey L., et al. "Characterization of surface Lymphotoxin Forms," J. Immunology 154:33–46 (1995).

Browning, Jeffrey L., et al., "Signaling through the Lymphotoxin Beta Receptor Induces the Death of Some Adenocarcinoma Tumor Lines," J. Exp. Med. 183 March : 867–87 (1996).
Cavender, Druie et al. "Pathways to chronic inflammation in rheumatoid synovitis," Federation Proceedings 46: 113–117 (1987).
Chisholm, Patricia L., et al., "Monoclonal antibodies to the intergrin ALPHA–4 subunit inhibit the murine contact hypersensitivity response," Eur. J. Immunology, 23: 682–688 (1993).
Crowe, Paul D., et al. "Production of lymphotoxin (Lt ALPHA) and a soluable dimeric form of its receptor using the baculovirus expression system," J. Immunology Methods, 168:79–89 (1994).
Crowe, Paul D., et al., "A Lymphotoxin–Beta–Specific Receptor", Science, 264:707–10 (1994).
DeTogni, Pietro, et al., "Abnormal Development of Peripheral Lymphoid Organs in Mice Difincient in Lymphotoxin," Science 264: 703–06 (1994).
Fagerstam, Lars G., et al., "Surface Plasmon Resonance Detection in Affinity Technologies," Handbook of Affinity Chromatography, pp. 229–252.
Gatanaga, Testsuya, "Purification and characerization of an inhibitor (soluble tumor necrosis factor receptor) for tumor necrosis factor and lymphotoxin obtained from the serum ultrafiltrates of human cancer patients." Proc. Natl. Acad. Sci. USA 87, pp 8781–8784 (1990).
Higuchi, Masahiro et al., "Inhibition of Ligand binding and Antiproliferative effects of Tumor Necrosis Factor and Lymphotoxin by Soluable Forms of Recombinant P60 and P80 Receptors," Biochemical and Biophysical Research Communication, vol. 182, No. 2, pp 638–643 (1992).
Jalkanen, S., et al., "A Distinct Endothelial Cell Recognition System That Controls Lymphocyte Traffic into inflamed Synovium," Science 233:556–558 (1986).
Katz, Jonathan D., et al., "T Helper Cell Subsets in Insulin–Dependent Diabetes," Science 268: 1185–1188 (1995).

(List continued on next page.)

Primary Examiner—Geetha P. Bansal
(74) Attorney, Agent, or Firm—Niki D. Cox, Esq.

(57) ABSTRACT

This invention relates to compositions and methods comprising "lymphotoxin-β receptor blocking agents", which block lymphotoxin-β receptor signalling. Lymphotoxin-β receptor blocking agents are useful for treating lymphocyte-mediated immunological diseases, and more particularly, for inhibiting Th1 cell-mediated immune responses. This invention relates to soluble forms of the lymphotoxin-β receptor extracellular domain that act as lymphotoxin-β receptor blocking agents. This invention also relates to the use of antibodies directed against either the lymphotoxin-β receptor or its ligand, surface lymphotoxin, that act as lymphotoxin-β receptor blocking agents. A novel screening method for selecting soluble receptors, antibodies and other agents that block LT-β receptor signalling is provided.

14 Claims, 7 Drawing Sheets

OTHER PUBLICATIONS

Lawton, Pornsri, et al., "Characterization of the Mouse Lymphotoxin–Beta–Gene," *J Immunol. 154*: 239–246 1995.

Modlin, Robert L. "Type 2 cytokines and negative immune regulation in human infections," *Current Opinion in Immunology 5*: 511–517 (1993).

Morrison, Sherrie L., "In Vitro Antibodies: Strategies for Production and Application," *Annu. Review Immunology*, 10: 339–365 (1992).

Peppel, Karsten, et al., "A Tumor Necrosis Factor (TNF) Receptor–IgG Heavy Chain Chimeric Protein as a Bivalent Antagonist of TNF Activity." *J. Exp. Med. 174*: 1483–1489.

Rennert, P.D., et al. "Normal Development of Lymph Nodes is Disrupted by Soluble LT beta Receptor—Ig Fusion Protein," *Eur. Cytokine Netw. vol. 7*, p16 (1996).

Renshaw, Blair R., et al. "Humoral Immune Responses in CD40 Ligand–deficient Mice," *J. Exp. Med. 180*: 1889–1900 (1994).

Romagnani, Sergio, "Lymphokine Production by Human T Cells in Disease States," *Annual Review Immunology 12*: 227–257 (1994).

Sayegh, Mohamed H., et al., "CD28–B7 Blockade after Alloantigenic Challenge in Vivo Inhibits Th1Cytokines but Spares Th2," *J. Exp. Med*, 181: 1869–1874 (1995).

Shehadeh, Naim N., et al., "Altered Cytokine Activity in Adjuvant Inhibition of Autoimmune Diabetes," *Journal of Autoimmunity 6*: 291–300 (1993).

Ware, C.F., et al., "The Ligands and Receptors of the Lymphotoxin System," *Pathways for Cytolysis*, pp. 175–218 (1995).

Ware, C.F., et al., "Expression of Surface Lymphotoxin and Tumor Necrosis Factor on Activated T, B and Natural Killer Cells," J. Immunol. 149: pp. 3881–3888 (1992).

Warzocha, Krzysztof, et al., "Mechanisms of actions of the tumor necrosis factor and lymphotoxin ligand–receptor system," *Eur. Cytokine Netw. vol. 5, No. 6*: pp. 83–96 (1994).

Zhou, M., et al., "Real–Time Measurements of Kinetics of EGF Binding to Soluble EGF Recptor Monomers and Dimers Support the Dimerization Model for Receptor Activation," *Biochem. 32*: 8193–8198 1993.

Ziff, Morris, "Emigration of Lymphocytes in Rheumatoid Synovitis," *Advances in Inflammation Research 12*: 1–9 (1988).

```
1    SQPQAVPPYA SENQTCRDQE KEYYEPQHRI CCSRCPPGTY VSAKCSRIRD    50
51   TVCATCAENS YNEHWNYLTI CQLCRPCDPV MGLEEIAPCT SKRKTQCRCQ   100
101  PGMFCAAWAL ECTHCELLSD CPPGTEAELK DEVGKGNNHC VPCKAGHFQN   150
151  TSSPSARCQP HTRCENQGLV EAAPGTAQSD TTCKNPLEPL PPEMSGT      197
```

FIG. 1

SOLUBLE LYMPHOTOXIN-β RECEPTOR AS A THERAPEUTIC AGENT FOR TREATING TH-1 CELL-ASSOCIATED AUTOIMMUNE DISEASE

This is a continuation application of U.S. Ser. No. 08/505,606 filed on Jul. 21, 1995, now U.S. Pat. No. 5,925,351. The entire disclosures of the aforesaid patent application is incorporated herein by reference.

TECHNICAL FIELD OF THE INVENTION

This invention relates to compositions and methods comprising "lymphotoxin-β receptor blocking agents", which block lymphotoxin-β receptor signalling. Lymphotoxin-β receptor blocking agents are useful for treating lymphocyte-mediated immunological diseases, and more particularly, for inhibiting Th1 cell-mediated immune responses. This invention relates to soluble forms of the lymphotoxin-β receptor extracellular domain that act as lymphotoxin-β receptor blocking agents. This invention also relates to the use of antibodies directed against either the lymphotoxin-β receptor or its ligand, surface lymphotoxin, that act as lymphotoxin-β receptor blocking agents. A novel screening method for selecting soluble receptors, antibodies and other agents that block LT-β receptor signalling is provided.

BACKGROUND OF THE INVENTION

The pattern of cytokines released at the onset of an immune challenge can affect the subsequent choice of which immune effector pathways are activated. The choice between immune effector mechanisms is mediated by CD4-positive helper T lymphocytes (T helper cells or Th cells). Th cells interact with antigen-presenting cells (APCs), which display peptide fragments of processed foreign antigen in association with MHC class II molecules on their surfaces. Th cells are activated when they recognize particular epitopes of a foreign antigen displayed on the appropriate APC surface for which the Th cells express a specific receptor. Activated Th cells, in turn, secrete cytokines (lymphokines) which activate appropriate immune effector mechanisms.

Th cells can activate diverse effector mechanisms, including killer T cell activation, B cell antibody production and macrophage activation. The choice between effector mechanisms is mediated largely by which cytokines are produced by the activated Th cells.

Th cells can be divided into three subgroups based on their cytokine secretion patterns (Fitch et al., Ann. Rev. Immunol., 11, pp. 29–48 (1993)). These subgroups are called Th0, Th1 and Th2. In the mouse, non-stimulated "naive" T helper cells produce IL-2. Short term stimulation leads to Th0 precursor cells, which produce a wide range of cytokines including IFN-γ, IL-2, IL-4, IL-5 and IL-10. Chronically-stimulated Th0 cells can differentiate into either Th1 or Th2 cell types, whereupon the cytokine expression pattern changes.

Some cytokines are released by both Th1 and Th2 cells (e.g., IL-3, GM-CSF and TNF). Other cytokines are made exclusively by one or the other Th cell subgroup. The specialized effects of T helper cell subgroups were first recognized in mouse. A similar subdivision of T helper cells also exists in humans (Romagnani et al., Ann. Rev. Immunol., 12, pp. 227–57 (1994)).

Th1 cells produce LT-α, IL-2 and IFN-γ. In humans, the Th1 pattern of cytokine secretion has been generally associated with cellular immunity and resistance to infection. The Th1 cytokines tend to activate macrophages and certain inflammatory responses such as Type IV "delayed type" hypersensitivity (see below). Th1 cytokines play an important role in cellular rejection of tissue grafts and organ transplants.

Th2 cells produce the cytokines IL-4, IL-5, IL-6 and IL-10. Th2 cytokines increase eosinophil and mast cell production and promote the full expansion and maturation of B cells (Howard et al., "T cell-derived cytokines and their receptors", Fundamental Immunology, 3d ed., Raven Press, New York (1993)). Th2 cytokines also enhance antibody production, including IgE antibodies associated with allergic responses and anti-graft antibodies. Th2 cells may also participate in immune suppression and tolerance to persistent antigens.

Th1- and Th2-associated cytokines play a role in certain hypersensitivity responses—inappropriate or disproportionate immune responses evoked upon contact with a previously encountered antigen. There are four recognized types of hypersensitivity (Roitt et al., Immunology, pp. 19.1–22.12 (Mosby-Year Book Europe Ltd., 3d ed. 1993)).

Type I "immediate hypersensitivity" involves allergen-induced Th2 cell activation and Th2 cytokine release. The Th2 cytokine IL-4 stimulates B cells to undergo isotype switching to produce IgE, which activates mast cells to produce acute inflammatory reactions such as those which lead to eczema, asthma and rhinitis.

Types II and III hypersensitivity are caused by IgG and IgM antibodies directed against cell surface or specific tissue antigens (Type II) or soluble serum antigens (Type III). These types of hypersensitivity reactions are not thought to be mediated by Th cells.

Type IV "delayed type" hypersensitivity (DTH) is Th1 cell mediated. DTH reactions take more than 12 hours to develop and are referred to as "cell-mediated" because they can be transferred between mice by transferring Th1 cells but not serum alone. Type IV DTH responses are generally classified into three types: contact, tuberculin-type and granulomatous hypersensitivity.

Many cell-mediated responses that can cause disease are inducible in healthy mice by transferring lymphocytes from a diseased mouse (e.g., insulin-dependent diabetes and experimental autoimmune encephalitis). This feature distinguishes Type IV DTH from the other three types of hypersensitivity, which are humoral immune responses caused primarily by antibodies which can be transferred in cell-free serum.

T helper cells also participate in the regulation of de novo immunoglobulin isotype switching. Different Th subsets may influence the relative proportion of immunoglobulins of a given isotype produced in response to immune challenge. For example, the Th2 cytokine IL-4 can switch activated B cells to the IgG1 isotype and suppress other isotypes. As discussed above, IL-4 also activates IgE overproduction in type I hypersensitivity reactions. The Th2 cytokine IL-5 induces the IgA isotype. These Th2 cytokine effects on isotype switching are counter-balanced by IFN-γ produced by Th1 cells.

The differential patterns of cytokines secreted by Th1 and Th2 cells appear to direct a response towards different immune effector mechanisms. The switch that activates either a cell-mediated or humoral effector mechanism is sensitized by cross-suppression between Th1 and Th2 cells: IFN-γ produced by Th1 cells inhibits Th2 cell proliferation and Th2 cell-secreted IL-10 appears to reduce cytokine secretion from Th1 cells.

Depending on the relative affinities of the cytokines for their molecular targets, Th1 and Th2 negative regulatory circuits may amplify the effects of small concentration differences-between Th1 and Th2 cytokines. An amplified Th1 or Th2 cytokine signal may trigger the switch between cell-mediated or humoral effector mechanisms based on small changes in the relative concentrations of Th1 and Th2 cytokines. The ability to control this switch by modulating the relative concentrations of Th1 and Th2 cytokines would be useful for treating imbalances in a variety of Th1 and Th2 cell-dependent immune responses which can lead to immune disorders and diseases.

Pathological Th1 responses are associated with a number of organ-specific and systemic autoimmune conditions, chronic inflammatory diseases, and delayed type hypersensitivity reactions. As discussed above, Th1 responses also contribute to cellular responses leading to grafted tissue and transplanted organ rejection. The treatment of these various Th1 cell-based immunological conditions generally employs immunomodulatory and immuno suppressive agents as well as a number of drugs with poorly characterized mechanisms (e.g., gold or penicillamine). Three general immunosuppressive agents used currently are steroids, cyclosporine and azathioprine.

Steroids are pleiotropic anti-inflammatory agents which suppress activated macrophages and inhibit the activity of antigen presenting cells in ways which reverse many of the effects of the Th1 cytokine IFN-$\gamma$. Cyclosporine—a potent immunosuppressive agent—suppresses cytokine production and reduces the expression of IL-2 receptors on lymphocytes during their activation. Azathioprine is an anti-proliferative agent which inhibits DNA synthesis. These non-specific immunosuppressive agents are generally required in high doses which increase their toxicity (e.g. nephro- and hepatotoxicity) and cause adverse side effects. They are thus unsuitable for long term therapies.

To address the problems caused by conventional treatments with non-specific immunosuppressive agents, many current therapeutic strategies aim at suppressing or activating selective aspects of the immune system. An especially attractive goal is the manipulation of the balance between Th1 and Th2 cytokines to shift the balance between cell-mediated and humoral effector mechanisms.

To accomplish a shift between cell-mediated and humoral effector mechanisms, it would be useful to be able to modulate the activity of a molecule that can shift the relative activities of Th1 and Th2 cell subclasses. Candidates for such molecules include the cytokines and their receptors. Recent data suggest that LT-$\alpha$, IL-12, IFN-$\alpha$ and IFN-$\gamma$ favor the development of Th1 responses, whereas IL-1 and IL-4 polarize a response towards a Th2 effector mechanism (Romagnani et al., *Ann. Rev. Immunol.*, 12, pp. 227–57 (1994)).

Many of the Th cell cytokines are pleiotropic regulators of immune development and function, and inhibiting their production would have deleterious effects on non-T cell mediated responses. A desirable and effective target for selectively modulating the choice between Th1 and Th2 effector mechanisms has not been identified.

SUMMARY OF THE INVENTION

The present invention solves the problems referred to above by providing pharmaceutical compositions and methods for treating immunological diseases by inhibiting lymphotoxin-$\beta$ receptor (LT-$\beta$-R) signalling using lymphotoxin-$\beta$ receptor blocking agents. More particularly, the compositions and methods comprising LT-$\beta$-R blocking agents are useful for inhibiting Th1 cell-mediated immune responses.

In one embodiment, soluble forms of the lymphotoxin-$\beta$ receptor extracellular domain that act as LT-$\beta$-R blocking agents are provided. The preferred compositions and methods of this embodiment comprise a recombinant lymphotoxin-$\beta$ receptor fusion protein that has the LT-$\beta$-R extracellular ligand binding domain fused to an immunoglobulin constant heavy chain domain. More preferably, the LT-$\beta$-R ligand binding domain is fused to a human IgG Fc domain.

In another embodiment of this invention, antibodies that act as LT-$\beta$-R blocking agents are provided. Preferred compositions and methods of this embodiment comprise one or more antibodies directed against the lymphotoxin-$\beta$ receptor. More preferably, the antibody is a monoclonal antibody. Other preferred compositions and methods of this embodiment comprise one or more antibodies directed against surface lymphotoxin. More preferably, the antibody is a monoclonal antibody directed against lymphotoxin-$\beta$.

This invention further provides a novel screening process for selecting LT-$\beta$-R blocking agents—such as soluble forms of the LT-$\beta$-R, anti-LT Abs and anti-LT-$\beta$-R Abs. This screening process involves performing tumor cell cytotoxicity assays that monitor LT-$\beta$-R signalling. The assay makes use of the increased sensitivity of human adenocarcinoma cells to ligand- or antibody-induced LT-$\beta$-R signalling in the presence of an LT-$\beta$-R activating agent (such as LT-$\alpha$1/$\beta$2) in a tumor cytotoxicity assay.

LT-$\beta$-R blocking agents inhibit the cytotoxic effects of LT-$\alpha$/$\beta$ heteromeric complexes (or other LT-$\beta$-R activating agents) on tumor cells. The procedure used to test putative LT-$\beta$-R blocking agents is exemplified for the case of anti-LT-$\beta$-R antibodies (in the presence of the LT-$\beta$-R activating agents LT-$\alpha$1/$\beta$2) and comprises the following steps:

1) Tumor cells (e.g., HT29 human adenocarcinoma cells) are cultured for several days in media containing IFN-$\gamma$ and purified LT-$\alpha$1/$\beta$2 in the presence or absence of the particular anti-LT-$\beta$-R Ab being assayed;

2) The cells are treated with a dye that stains living cells; and

3) The number of stained cells is quantitated to determine the fraction of tumor cells killed in the presence of LT-$\alpha$1/$\beta$2, IFN-$\gamma$ and the test anti-LT-$\beta$-R Ab in each sample. Alternatively, the number of surviving cells can be determined by any of a number of well-known assays which measure cell viability, such as $^3$H-thymidine incorporation into DNA. An anti-LT-$\beta$-R Ab (or an Ab combination) that decreases the percentage of tumor cells killed in this assay by at least 20% is a LT-$\beta$-R blocking agent within the scope of this invention.

This cytolytic assay may be performed using LT-$\alpha$/$\beta$ heteromeric complexes and other LT-$\beta$-R activating agents, either alone or in combination. The assay can also be adapted as required to identify new LT-$\beta$-R blocking agents.

BRIEF DESCRIPTION OF THE DRAWINGS

FIG. 1. The sequence of the extracellular portion of the human LT-$\beta$ receptor which encodes the ligand binding domain.

DETAILED DESCRIPTION OF THE INVENTION

Figure 2:
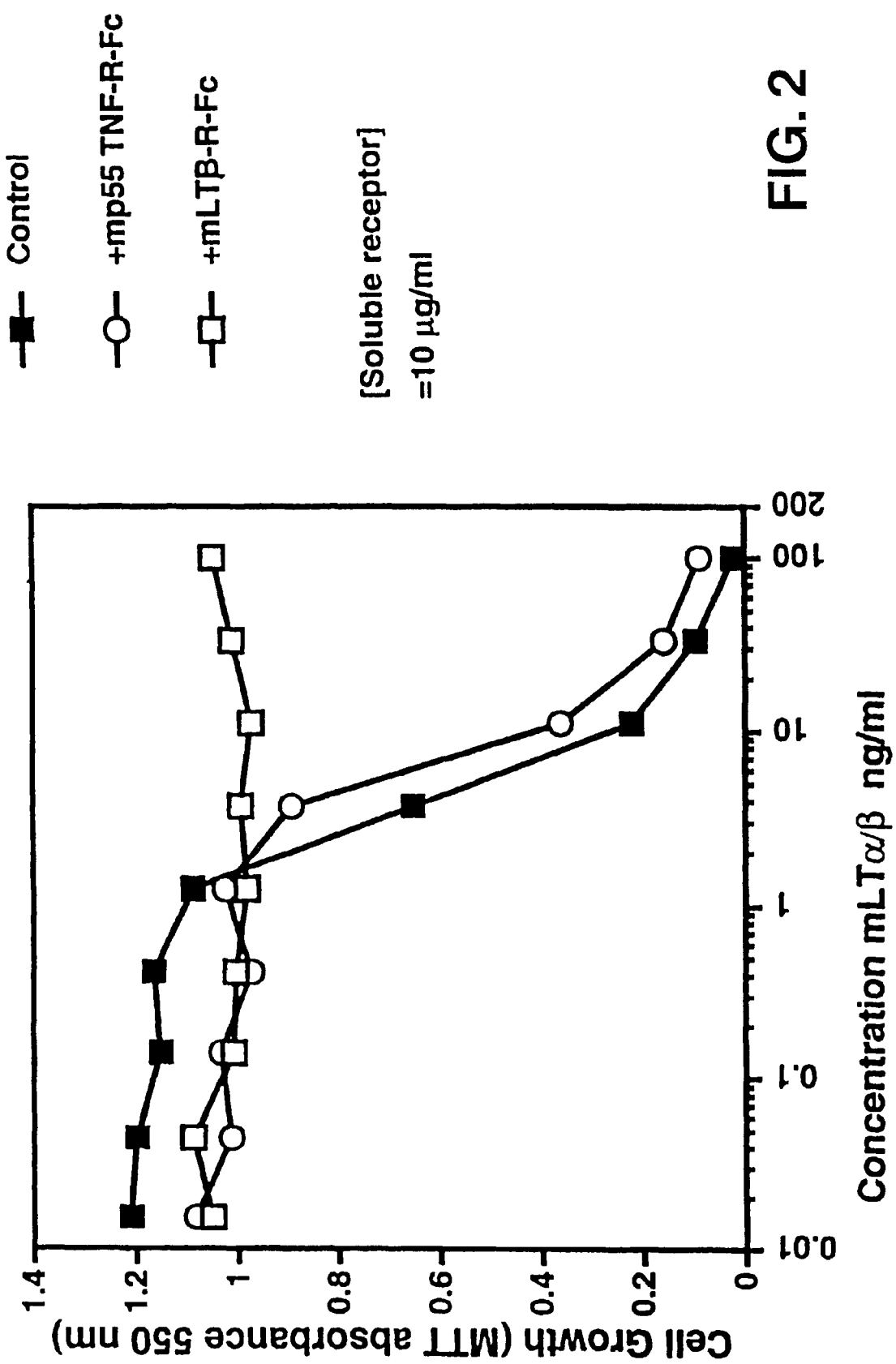
FIG. 2. A soluble murine LT-$\beta$ receptor coupled to the human IgG1 Fc domain (mLT-$\beta$-R-Fc) blocks LT-$\beta$-R signalling in mouse WEHI 164 cells induced by soluble murine LT-α/β ligand. WEHI 164 cells are killed as a function of increasing LT ligand (mLT-α/β) concentration. Soluble mLT-β-R-Fc (10 μg/ml) blocks this LT ligand-induced cell death. A soluble murine TNF receptor fusion protein (p55TNF-R-Fc) has little effect on blocking LT-α/β-activated cell death. Growth was quantitated after three days by measuring the optical density (OD 550) of reacted MTT, which is proportional to cell number.

In order that the invention herein described may be fully understood, the following detailed description is set forth.

The term "cytokine" refers to a molecule which mediates interactions between cells. A "lymphokine" is a cytokine released by lymphocytes.

The term "T helper (Th) cells" refers to a functional subclass of T cells which help to generate cytotoxic T cells and which cooperate with B cells to stimulate antibody production. Helper T cells recognize antigen in association with class II MHC molecules.

The term "Th1" refers to a subclass of T helper cells that produce LT-α, interferon-γ and IL-2 (and other cytokines) and which elicit inflammatory reactions associated with a cellular, i.e. non-immunoglobulin, response to a challenge.

The term "Th2" refers to a subclass of T helper cells that produce cytokines, including IL-4, IL-5, IL-6 and IL-10, which are associated with an immunoglobulin (humoral) response to an immune challenge.

The term "cell mediated" refers to those immunological events that result from the direct effects of T cells and their products to produce a response. This type of response is generally (but not exclusively) associated with the Th1 class of T cells. Not included in this category would be the helper effects of T cells on β cell differentiation and B cell expansion, which are generally associated with the Th2 class of T cells.

The term "delayed type hypersensitivity (DTH)" refers to an immunological response that is characterized by a slow response to an antigen with the full effect manifesting itself over a 1–3 day period. This slow response is in contrast to the relatively fast response seen in an immunoglobulin-mediated (humoral) allergic reaction. There are three types of DTH reactions: contact hypersensitivity, tuberculin-type hypersensitivity and granulomatous reactions.

The terms "immunoglobulin response" or "humoral response" refer to the immunological response of an animal to a foreign antigen whereby the animal produces antibodies to the foreign antigen. The Th2 class of T helper cells are critical to the efficient production of high affinity antibodies.

The term "Fc domain" of an antibody refers to a part of the molecule comprising the hinge, CH2 and CH3 domains, but lacking the antigen binding sites. The term is also meant to include the equivalent regions of an IgM or other antibody isotype.

The term "anti-LT-β receptor antibody" refers to any antibody that specifically binds to at least one epitope of the LT-β receptor.

The term "anti-LT antibody" refers to any antibody that specifically binds to at least one epitope of LT-α, LT-β or a LT-α/β complex.

The term "LT-β-R signalling" refers to molecular reactions associated with the LT-β-R pathway and subsequent molecular reactions which result therefrom.

The term "LT-β-R blocking agent" refers to an agent that can diminish ligand binding to LT-β-R, cell surface LT-β-R clustering or LT-β-R signalling, or that can influence how the LT-β-R signal is interpreted within the cell.

A LT-β-R blocking agent that acts at the step of ligand-receptor binding can inhibit LT ligand binding to the LT-β-R by at least 20%. A LT-β-R blocking agent that acts after the step of ligand-receptor binding can inhibit the cytotoxic effects of LT-β-R activation on a tumor cell by at least 20%. Examples of LT-β-R blocking agents include soluble LT-β-R-Fc molecules, and anti-LT-α, anti-LT-β, anti-LT-α/β and anti-LT-β-R Abs. Preferably, the antibodies do not cross-react with the secreted form of LT-α.

The term "LT-β-R biological activity" refers to: 1) the ability of the LT-β-R molecule or derivative to compete for soluble or surface LT ligand binding with soluble or surface LT-β-R molecules; or 2) the ability to stimulate an immune regulatory response or cytotoxic activity in common with a native LT-β-R molecule.

The terms "LT-α/β heteromeric complex" and "LT heteromeric complex" refer to a stable association between at least one LT-α and one or more LT-β subunits, including soluble, mutant, altered and chimeric forms of one or more of the subunits. The subunits can associate through electrostatic, van der Waals, or covalent interactions. Preferably, the LT-α/β heteromeric complex has at least two adjacent LT-β subunits and lacks adjacent LT-αsubunits. When the LT-α/β heteromeric complex serves as a LT-β-R activating agent in a cell growth assay, the complex is preferably soluble and has the stoichiometry LT-α1/β2.

Soluble LT-α/β heteromeric complexes lack a transmembrane domain and can be secreted by an appropriate host cell which has been engineered to express LT-α and/or LT-β subunits (Crowe et al., *J. Immunol. Methods,* 168, pp. 79–89 (1994)).

The term "LT ligand" refers to a LT heteromeric complex or derivative thereof that can specifically bind to the LT-β receptor.

The term "LT-β-R ligand binding domain" refers to the portion or portions of the LT-β-R that are involved in specific recognition of and interaction with a LT ligand.

The terms "surface LT-α/β complex" and "surface LT complex" refer to a complex comprising LT-α and membrane-bound LT-β subunits—including mutant, altered and chimeric forms of one or more of the subunits—which is displayed on the cell surface. "Surface LT ligand" refers to a surface LT complex or derivative thereof that can specifically bind to the LT-β receptor.

The term "subject" refers to an animal, or to one or more cells derived from an animal. Preferably, the animal is a mammal. Cells may be in any form, including but not limited to cells retained in tissue, cell clusters, immortalized, transfected or transformed cells, and cells derived from an animal that have been physically or phenotypically altered.

Lymphotoxin-β: A Member of the TNF Family

Tumor Necrosis Factor (TNF)-related cytokines have emerged as a large family of pleiotropic mediators of host defense and immune regulation. Members of this family exist in membrane-bound forms which act locally through cell-cell contact, or as secreted proteins which can act on distant targets. A parallel family of TNF-related receptors react with these cytokines and trigger a variety of pathways including cell death, cell proliferation, tissue differentiation and proinflammatory responses.

TNF, lymphotoxin-α (LT-α, also called TNF-β) and lymphotoxin-β (LT-β) are members of the TNF family of ligands, which also includes the ligands to the Fas, CD27, CD30, CD40, OX-40 and 4-1BB receptors (Smith et al., *Cell,* 76, pp. 959–62 (1994)). Signalling by several members of the TNF family—including TNF, LT-α, LT-β and Fas—can induce tumor cell death by necrosis or apoptosis (programmed cell death). In non-tumorigenic cells, TNF and many of the TNF family ligand-receptor interactions influence immune system development and responses to various immune challenges.

Most TNF family ligands are found as a membrane-bound form on the cell surface. TNF and LT-α are found in both secreted and membrane-associated surface forms in humans. Surface TNF has a transmembrane region that is proteolytically cleaved to generate the secreted form. In contrast, surface LT-α lacks a transmembrane region. Membrane-associated LT-α is tethered to the cell surface as a heteromeric complex with LT-β, a related transmembrane polypeptide, in a LT-α/β complex.

Most membrane-associated LT-α/β complexes ("surface LT") have a LT-α1/β2 stoichiometry (Browning et al., *Cell,* 72, pp. 847–56 (1993); Browning et al., *J. Immunol.,* 154, pp. 33–46 (1995)). Surface LT ligands do not bind TNF-R with high affinity and do not activate TNF-R signalling. Another TNF-related receptor, called the LT-β receptor (LT-β-R), binds these surface lymphotoxin complexes with high affinity (Crowe et al., *Science,* 264, pp. 707–10 (1994)).

LT-β-R signalling, like TNF-R signalling, has anti-proliferative effects and can be cytotoxic to tumor cells. In applicants' co-pending U.S. application Ser. No. 08/378,968, compositions and methods for selectively stimulating LT-β-R using LT-β-R activating agents are disclosed. LT-β-R activating agents are useful for inhibiting tumor cell growth without co-activating TNF-R-induced proinflammatory or immunoregulatory pathways.

In non-tumor cells, TNF and TNF-related cytokines are active in a wide variety of immune responses. Both TNF and LT-α ligands bind to and activate TNF receptors (p55 or p60 and p75 or p80; herein called "TNF-R"). TNF and LT-α are produced by macrophages in an early and rapid response to microbial infection which enhances the microbicidal activity of macrophages and neutrophils. TNF and LT-α made by macrophages or cytotoxic T lymphocytes (CTLs or "killer T cells") bind to TNF receptors on target cell surfaces and trigger the death of susceptible cells.

TNF and TNF-related cytokines can also initiate inflammatory cascades in response to infection or stress. The release of TNF, LT-α and IFN-γ changes the adhesion properties between the vascular endothelial cells and certain lymphocyte types. Increased adhesion facilitates phagocyte and leucocyte migration from the bloodstream into the tissues surrounding an inflammation site. Similar inflammatory reactions play a major role in cellular rejection of tissue grafts and organ transplants, and in certain immune disorders.

Cell surface lymphotoxin (LT) complexes have been characterized in $CD4^+$ T cell hybridoma cells (II-23.D7) which express high levels of LT (Browning et al., *J. Immunol.,* 147, pp. 1230–37 (1991); Androlewicz et al., *J. Biol. Chem.,* 267, pp. 2542–47 (1992)). The expression and biological roles of LT-β-R, LT subunits and surface LT complexes have been reviewed in C.F. Ware et al., "The ligands and receptors of the lymphotoxin system", in *Pathways for Cytolysis. Current Topics Microbiol. Immunol.,* Springer-Verlag, pp. 175–218 (1995).

LT-α expression is induced and LT-α secreted primarily by activated T and B lymphocytes and natural killer (NK) cells. Among the T helper cell subclasses, LT-α appears to be produced by Th1 but not Th2 cells. LT-α has also been detected in melanocytes. Microglia and T cells in lesions of multiple sclerosis patients can also be stained with anti-LT-α antisera.

Lymphotoxin-β (also called p33), has been identified on the surface of T lymphocytes, T cell lines, B cell lines and lymphokine-activated killer (LAK) cells. LT-β is the subject of applicants' co-pending international applications PCT/US91/04588, published Jan. 9, 1992 as WO 92/00329; and PCT/US93/11669, published June 23, 1994 as WO 94/13808, which are herein incorporated by reference.

Surface LT complexes are primarily expressed by activated T and β lymphocytes and natural killer (NK) cells as defined by FACS analysis or immunohistology using anti-LT-α antibodies or soluble LT-β-R-Fc fusion proteins. Surface LT has also been described on human cytotoxic T lymphocyte (CTL) clones, activated peripheral mononuclear lymphocytes (PML), IL-2-activated peripheral blood lymphocytes (LAK cells), pokeweed mitogen-activated or anti-CD40-activated peripheral B lymphocytes (PBL) and various lymphoid tumors of T and B cell lineage. Engagement of alloantigen-bearing target cells specifically induces surface LT expression by CD8$^+$ and CD4$^+$ CTL clones.

The LT-β receptor, a member of the TNF family of receptors, specifically binds to surface LT ligands. LT-β-R binds LT heteromeric complexes (predominantly LT-α1/β2 and LT-α2/β1) but does not bind TNF or LT-α (Crowe et al., Science, 264, pp. 707–10 (1994)). Signalling by LT-β-R may play a role in peripheral lymphoid organ development and in humoral immune responses.

Studies on LT-β-R expression are in their early stages. LT-β-R mRNAs are found in human spleen, thymus and other major organs. LT-β-R expression patterns are similar to those reported for p55-TNF-R except that LT-β-R is lacking on peripheral blood T cells and T cell lines.

Production of Soluble LT Complexes

Soluble LT-α/β heteromeric complexes comprise LT-β subunits which have been changed from a membrane-bound to a soluble form. These complexes are described in detail in applicants' co-pending international application (PCT/US93/11669, published June 23, 1994 as WO 94/13808). Soluble LT-β peptides are defined by the amino acid sequence of lymphotoxin-β wherein the sequence is cleaved at any point between the end of the transmembrane region (i.e. at about amino acid #44) and the first TNF homology region (i.e. at amino acid #88) according to the numbering system of Browning et al., Cell, 72, pp. 847–56 (1993).

Soluble LT-β polypeptides may be produced by truncating the N-terminus of LT-β to remove the cytoplasmic tail and transmembrane region (Crowe et al., Science, 264, pp. 707–710 (1994)). Alternatively, the transmembrane domain may be inactivated by deletion, or by substitution of the normally hydrophobic amino acid residues which comprise a transmembrane domain with hydrophilic ones. In either case, a substantially hydrophilic hydropathy profile is created which will reduce lipid affinity and improve aqueous solubility. Deletion of the transmembrane domain is preferred over substitution with hydrophilic amino acid residues because it avoids introducing potentially immunogenic epitopes.

The deleted or inactivated transmembrane domain may be replaced with or attached to a type I leader sequence (e.g. the VCAM-1 leader) such that the protein is secreted beginning with a sequence anywhere from between val40 to pro88. Soluble LT-β polypeptides may include any number of well-known leader sequences at the N-terminus. Such a sequence would allow the peptides to be expressed and targeted to the secretion pathway in a eukaryotic system. See, e.g., Ernst et al., U.S. Pat. No. 5,082,783 (1992).

Soluble LT-α/β heteromeric complexes may be produced by co-transfecting a suitable host cell with DNA encoding LT-α and soluble LT-β (Crowe et al., J. Immunol. Methods, 168, pp. 79–89 (1994)). Soluble LT-β secreted in the absence of LT-α is highly oligomerized. However, when co-expressed with LT-α, a 70 kDa trimeric-like structure is formed which contains both proteins. It is also possible to produce soluble LT-α1/β2 heteromeric complexes by transfecting a cell line which normally expresses only LT-α (such as the RPMI 1788 cells discussed above) with a gene encoding a soluble LT-β polypeptide.

LT-α and LT-β polypeptides may be separately synthesized, denatured using mild detergents, mixed together and renatured by removing the detergent to form mixed LT heteromeric complexes which can be separated (see below).

Purification of LT-α1/β2 Complexes

Soluble LT-α1/β2 heteromeric complexes are separated from co-expression complexes comprising a different subunit stoichiometry by. chromatography using TNF and LT-β receptors as affinity purification reagents. The TNF receptors only bind within β/β clefts of LT complexes. The LT-β receptor binds with high affinity to β/β clefts, and with lower affinity to α/β clefts of heteromeric LT-α/β complexes.

Accordingly, LT-α3 and LT-α2/β1 will bind to TNF-R. The LT-β-R can also bind LT-α2/β1 trimers (within the α/β clefts) but cannot bind LT-α3. In addition, the LT-β-R (but not TNF-R) binds LT-α1/β2 and LT-βn (the exact composition of such preparation is unknown, however, they are large aggregates).

The receptor affinity reagents can be prepared as either a soluble extracellular domain (see for example Loetscher et al., J. Biol. Chem., 266, pp. 18324–29 (1991)), or as chimeric proteins with the extracellular ligand binding domain coupled to an immunoglobulin Fc domain (Loetscher et al., J. Biol. Chem., 266, pp. 18324–29 (1991); Crowe et al., Science, 264, pp. 707–710 (1994)). Receptors are coupled to affinity matrices by chemical cross-linking using routine procedures.

There are two schemes by which the LT-α1/β2 ligand can be purified using receptors and immuno-affinity chromatography. In the first scheme, a supernatant from an appropriate expression system co-expressing both LT-α and the truncated LT-β form is passed over a TNF-R column. The TNF-R will bind LT-α3 and LT-α2/β1 trimers. The flow through from the TNF-R column will contain LT-β(n) and LT-α1/β2.

In the second scheme, all LT-β-containing forms (LT-β(n), LT-α1/β2 and LT-α2/β1) are bound to and eluted from a LT-β-R column using classical methods such as chaotrophe or pH change. (LT-α3 flows through this column). The eluate is neutralized or the chaotrophe removed, and the eluate is then passed over a TNF-R column, which binds only to the LT-α2/β1 trimers. The flow through of this column will contain LT-β (n) and LT-α1/β2 trimers.

In both cases, pure LT-α1/β2 trimers can be separated from LT-β by subsequent gel filtration and/or ion exchange chromatographic procedures known to the art.

Alternatively, different forms of LT-α/β heteromeric complexes can be separated and purified by a variety of conventional chromatographic means. It may also be preferable to combine a series of conventional purification schemes with one of the immunoaffinity purification steps described above.

Screening For LT-β-R Blocking Agents

In one embodiment of this invention, the LT-β-R blocking agent comprises an antibody (Ab) directed against LT-β-R that inhibits LT-β-R signalling. Preferably, the anti-LT-β-R Ab is a monoclonal antibody (mAb). One such inhibitory anti-LT-β-R mAb is BDA8 mAb.

Inhibitory anti-LT-β-R Abs and other LT-β-R blocking agents can be identified using screening methods that detect the ability of one or more agents either to bind to the LT-β-R or LT ligand, or to inhibit the effects of LT-β-R signalling on cells.

One screening method makes use of the cytotoxic effects of LT-β-R signalling on tumor cells bearing the LT-β-R. Tumor cells are exposed to one or more LT-β-R activating agents to induce LT-β-R signalling. LT-β-R activating agents include LT-α/β heteromeric complexes (preferably soluble LT-α1/β2) in the presence of IFN-γ, or an activating anti-LT-β-R Ab (see below; also described in applicants' co-pending U.S. application Ser. No. 08/378,968).

Antibodies and other agents that can block LT-β-R signalling are selected based on their ability to inhibit the cytotoxic effect of LT-β-R signalling on tumor cells in the following assay:

1) Tumor cells such as HT29 cells are cultured for three to four days in a series of tissue culture wells containing media and at least one LT-β-R activating agent in the presence or absence of serial dilutions of the agent being tested;
2) A vital dye stain which measures mitochondrial function such as MTT is added to the tumor cell mixture and reacted for several hours;
3) The optical density of the mixture in each well is quantitated at 550 nm wavelength light (OD 550). The OD 550 is proportional to the number of tumor cells remaining in the presence of the LT-β-R activating agent and the test LT-β-R blocking agent in each well. An agent or combination of agents that can reduce LT-β-R-activated tumor cell cytotoxicity by at least 20% in this assay is a LT-β-R blocking agent within the scope of this invention.

Any agent or combination of agents that activate LT-β-R signalling can be used in the above assay to identify LT-β-R blocking agents. LT-β-R activating agents that induce LT-β-R signalling (such as activating anti-LT-β-R mAbs) can be selected based on their ability—alone or in combination with other agents—to potentiate tumor cell cytotoxicity using the tumor cell assay described above.

Another method for selecting an LT-β-R blocking agent is to monitor the ability of the putative agent to directly interfere with LT ligand-receptor binding. An agent or combination of agents that can block ligand-receptor binding by at least 20% is an LT-β-R blocking agent within the scope of this invention.

Any of a number of assays that measure the strength of ligand-receptor binding can be used to perform competition assays with putative LT-β-R blocking agents. The strength of the binding between a receptor and ligand can be measured using an enzyme-linked immunoadsorption assay (ELISA) or a radio-immunoassay (RIA). Specific binding may also be measured by fluorescently labelling antibody-antigen complexes and performing fluorescence-activated cell sorting (FACS) analysis, or by performing other such immunodetection methods, all of which are techniques well known in the art.

The ligand-receptor binding interaction may also be measured with the BIAcore™ instrument (Pharmacia Biosensor) which exploits plasmon resonance detection (Zhou et al., *Biochemistry*, 32, pp. 8193–98 (1993); Faegerstram and O'Shannessy, "Surface plasmon resonance detection in affinity technologies", in *Handbook of Affinity Chromatography*, pp. 229–52, Marcel Dekker, Inc., New York (1993)).

The BIAcore™ technology allows one to bind receptor to a gold surface and to flow ligand over it. Plasmon resonance detection gives direct quantitation of the amount of mass bound to the surface in real time. This technique yields both on and off rate constants and thus a ligand-receptor dissociation constant and affinity constant can be directly determined in the presence and absence of the putative LT-β-R blocking agent.

With any of thesevor other techniques for measuring receptor-ligand interactions, one can evaluate the ability of a LT-β-R blocking agent, alone or in combination with other agents, to inhibit binding of surface or soluble LT ligands to surface or soluble LT-β-R molecules. Such assays may also be used to test LT-β-R blocking agents or derivatives of such agents (e.g. fusions, chimeras, mutants, and chemically altered forms)—alone or in combination—to optimize the ability of that altered agent to block LT-β-R activation.

Production of Soluble LT-β-R Molecules

The LT-β-R blocking agents in one embodiment of this invention comprise soluble LT-β receptor molecules. FIG. 1 shows the sequence of the extracellular portion of the human LT-β-R, which encodes the ligand binding domain. Using the sequence information in FIG. 1 and recombinant DNA techniques well known in the art, functional fragments encoding the LT-β-R ligand binding domain can be cloned into a vector and expressed in an appropriate host to produce a soluble LT-β-R molecule. Soluble LT-β-R molecules that can compete with native LT-β receptors for LT ligand binding according to the assays described herein are selected as LT-β-R blocking agents.

A soluble LT-β receptor comprising amino acid sequences selected from those shown in FIG. 1 may be attached to one or more heterologous protein domains ("fusion domain") to increase the in vivo stability of the receptor fusion protein, or to modulate its biological activity or localization.

Preferably, stable plasma proteins—which typically have a half-life greater than 20 hours in the circulation—are used to construct the receptor fusion proteins. Such plasma proteins include but are not limited to: immunoglobulins, serum albumin, lipoproteins, apolipoproteins and transferrin. Sequences that can target the soluble LT-β-R molecule to a particular cell or tissue type may also be attached to the LT-β-R ligand binding domain to create a specifically-localized soluble LT-β-R fusion protein.

All or a functional portion of the LT-β-R extracellular region (FIG. 1) comprising the LT-β-R ligand binding domain may be fused to an immunoglobulin constant region like the Fc domain of a human IgG1 heavy chain (Browning et al., *J. Immunol.*, 154, pp. 33–46 (1995)). Soluble receptor-IgG fusion proteins are common immunological reagents and methods for their construction are known in the art (see e.g., U.S. Pat. No. 5,225,538).

A functional LT-β-R ligand binding domain may be fused to an immunoglobulin (Ig) Fc domain derived from an immunoglobulin class or subclass other than IgG1. The Fc domains of antibodies belonging to different Ig classes or subclasses can activate diverse secondary effector functions. Activation occurs when the Fc domain is bound by a cognate Fc receptor. Secondary effector functions include the ability to activate the complement system, to cross the placenta, and to bind various microbial proteins. The properties of the different classes and subclasses of immunoglobulins are described in Roitt et al., *Immunology*, p. 4.8 (Mosby-Year Book Europe Ltd., 3d ed. 1993).

Activation of the complement system initiates cascades of enzymatic reactions that mediate inflammation. The products of the complement system have a variety of functions, including binding of bacteria, endocytosis, phagocytosis, cytotoxicity, free radical production and solubilization of immune complexes.

The complement enzyme cascade can be activated by the Fc domains of antigen-bound IgG1, IgG3 and IgM antibodies. The Fc domain of IgG2 appears to be less effective, and the Fc domains of IgG4, IgA, IgD and IgE are ineffective at activating complement. Thus one can select a Fc domain based on whether its associated secondary effector functions are desirable for the particular immune response or disease being treated with the LT-β-R-Fc fusion protein.

If it would be advantageous to harm or kill the LT ligand-bearing target cell, one could select an especially active Fc domain (IgG1) to make the LT-β-R-Fc fusion protein. Alternatively, if it would be desirable to target the LT-β-R-Fc fusion to a cell without triggering the complement system, an inactive IgG4 Fc domain could be selected.

Mutations in Fc domains that reduce or eliminate binding to Fc receptors and complement activation have been described (S. Morrison, *Annu. Rev. Immunol.*, 10, pp. 239–65 (1992)). These or other mutations can be used, alone or in combination, to optimize the activity of the Fc domain used to construct the LT-β-R-Fc fusion protein.

The production of a soluble human LT-β-R fusion protein comprising ligand binding sequences fused to a human immunoglobulin Fc domain (hLT-β-R-Fc) is described in Example 1. One CHO line made according to Example 1 that secretes hLT-β-R-Fc is called "hLTβ;R-hG1 CHO#14". A sample of this line was deposited on Jul. 21, 1995 with the American Type Culture Collection (ATCC) (Rockville, Md.) according to the provisions of the Budapest Treaty and was assigned the ATCC accession number.

The production of a,soluble murine LT-β-R fusion molecule (mLT-β-R-Fc) is described in Example 2. A CHO line made according to Example 2 that secretes mLT-β-R-Fc is called "mLTβ;R-hG1 CHO#1.3.BB". A sample of this line was deposited on Jul. 21, 1995 with the American Type Culture Collection (ATCC) (Rockville, Md.) according to the provisions of the Budapest Treaty and was assigned the ATCC accession number.

All restrictions on the availability to the public of the above ATCC deposits will be irrevocably removed upon the granting of a patent on this application.

Different amino acid residues forming the junction point of the receptor-Ig fusion protein may alter the structure, stability and ultimate biological activity of the soluble LT-β receptor fusion protein. One or more amino acids may be added to the C-terminus of the selected LT-β-R fragment to modify the junction point with the selected fusion domain.

The N-terminus of the LT-β-R fusion protein may also be varied by changing the position at which the selected LT-β-R DNA fragment is cleaved at its 5' end for insertion into the recombinant expression vector. The stability and activity of each LT-β-R fusion protein may be tested and optimized using routine experimentation and the assays for selecting LT-β-R blocking agents described herein.

Using the LT-β-R ligand binding domain sequences within the extracellular domain shown in FIG. 1, amino acid sequence variants may also be constructed to modify the affinity of the soluble LT-β receptor or fusion protein for LT ligand. The soluble LT-β-R molecules of this invention can compete for surface LT ligand binding with endogenous cell surface LT-β receptors. It is envisioned that any soluble molecule comprising a LT-β-R ligand binding domain that can compete with cell surface LT-β receptors for LT ligand binding is a LT-β-R blocking agent that falls within the scope of the present invention.

Soluble LT-β-R Molecules As LT-β-R Blocking Agents

A soluble human LT-β receptor-immunoglobulin fusion protein (hLT-β-R-Fc) was made according to the procedures in Example 1 and tested for its ability to block LT-β-R-induced cytotoxicity in human HT29 tumor cells. Table 1 (Example 3) compares the ability of soluble LT-β receptor (hLT-β-R-Fc) and TNF receptor (p55-TNF-R-Fc) fusion proteins to block the inhibitory effects of various TNF and soluble LT ligands on HT29 tumor cell growth.

The data in Table 1 indicate the concentrations at which a soluble LT-β receptor (hLT-β-R-Fc) can block the tumor cell death caused by interaction between LT-α1/β2 ligand and cell surface LT-β receptors by 50%. The ability to block tumor cell growth at least 20% identifies this soluble LT-β receptor as a LT-β-R blocking agent according to this invention. As expected, the soluble TNF-R fusion protein (p55-TNF-R-Fc) completely blocked TNF-induced growth inhibition by binding to TNF and preventing its interaction with surface receptor.

The soluble TNF-R fusion protein had no effect on LT ligand (LT-α1/β2)-mediated anti-proliferative effects. In contrast, the LT-β-R fusion protein blocked LT ligand effects but not the effects of TNF or LT-α. Thus soluble human LT-β-R fusion proteins do not interfere with TNF-R activation by TNF and LT-α ligands.

To determine whether LT-β-R signalling is also cytotoxic to tumor cells in mice, and whether soluble LT-β-R fusion proteins can block LT-β-R-induced cytotoxicity, a similar experiment was performed using mouse tumor cells. A soluble murine LT-β-R-Fc fusion protein (mLT-β-R-Fc; see Example 2) was tested for its ability to block the death of mouse WEHI 164 cells treated with LT ligand (Example 4).

FIG. 2 shows the effects of the soluble murine LT-β-R (mLT-β-R-Fc) on LT ligand-induced LT-β-R signalling in mouse WEHI 164 cells. As this assay indicates, WEHI 164 cells are killed by treatment with soluble LT-α1/β2 ligand. Addition of mLT-β-R-Fc blocks LT ligand-activated cell death. The control TNF receptor fusion protein (p55TNF-R-Fc) has little effect on blocking cell death.

These data show that a soluble LT-β-R fusion protein can effectively compete with surface LT-β-R molecules for LT ligand binding. The soluble mLT-β-R-Fc fusion protein thus acts as a LT-β-R blocking agent in mice.

Source of Anti-Human LT-β-R Antibodies

In another embodiment of this invention, antibodies directed against the human LT-β receptor (anti-LT-β-R Abs) function as LT-3-R blocking agents. The anti-LT-β-R Abs of this invention can be polyclonal or monoclonal (mAbs) and can be modified to optimize their ability to block LT-β-R signalling, their in vivo bioavailability, stability, or other desired traits.

Polyclonal antibody sera directed against the human LT-β receptor are prepared using conventional techniques by injecting animals such as goats, rabbits, rats, hamsters or mice subcutaneously with a human LT-β receptor-Fc fusion protein (Example 1) in complete Freund's adjuvant, followed by booster intraperitoneal or subcutaneous injection in incomplete Freund's. Polyclonal antisera containing the desired antibodies directed against the LT-β receptor are screened by conventional immunological procedures.

Mouse monoclonal antibodies (mAbs) directed against a human LT-β receptor-Fc fusion protein are prepared as described in Example 5. A hybridoma cell line (BD.A8.AB9) which produces the mouse anti-human LT-β-R mAb BDA8 was deposited on Jan. 12, 1995 with the American Type Culture Collection (ATCC) (Rockville, Md.) according to the provisions of the Budapest Treaty, and was assigned the ATCC accession number HB11798. All restrictions on the availability to the public of the above ATCC deposits will be irrevocably removed upon the granting of a patent on this application.

Various forms of anti-LT-β-R antibodies can also be made using standard recombinant DNA techniques (Winter and Milstein, Nature, 349, pp. 293–99 (1991)). For example, "chimeric" antibodies can be constructed in which the antigen binding domain from an animal antibody is linked to a human constant domain (e.g.

Cabilly et al., U.S. Pat. No. 4,816,567; Morrison et al., Proc. Natl. Acad. Sci. U.S.A., 81, pp. 6851–55 (1984)). Chimeric antibodies reduce the observed immunogenic responses elicited by animal antibodies when used in human clinical treatments.

In addition, recombinant "humanized antibodies" which recognize the LT-β-R can be synthesized. Humanized antibodies are chimeras comprising mostly human IgG sequences into which the regions responsible for specific antigen-binding have been inserted (e.g. WO 94/04679). Animals are immunized with the desired antigen, the corresponding antibodies are isolated, and the portion of the variable region sequences responsible for specific antigen binding are removed. The animal-derived antigen binding regions are then cloned into the appropriate position of human antibody genes in which the antigen binding regions have been deleted. Humanized antibodies minimize the use of heterologous (inter-species) sequences in human antibodies, and are less likely to elicit immune responses in the treated subject.

Construction of different classes of recombinant anti-LT-β-R antibodies can also be accomplished by making chimeric or humanized antibodies comprising the anti-LT-β-R variable domains and human constant domains (CH1, CH2, CH3) isolated from different classes of immunoglobulins. For example, anti-LT-β-R IgM antibodies with increased antigen binding site valencies can be recombinantly produced by cloning the antigen binding site into vectors carrying the human $\mu$ chain constant regions (Arulanandam et al., J. Exp. Med., 177, pp. 1439–50 (1993); Lane et al., Eur. J. Immunol., 22, pp. 2573–78 (1993); Traunecker et al., Nature, 339, pp. 68–70 (1989)).

In addition, standard recombinant DNA techniques can be used to alter the binding affinities of recombinant antibodies with their antigens by altering amino acid residues in the vicinity of the antigen binding sites. The antigen binding affinity of a humanized antibody can be increased by mutagenesis based on molecular modelling (Queen et al., i Proc. Natl. Acad. Sci. U.S.A., 86, pp. 10029–33 (1989); WO 94/04679).

It may be desirable to increase or to decrease the affinity of anti-LT-β-R Abs for the LT-β-R depending on the targeted tissue type or the particular treatment schedule envisioned. For example, it may be advantageous to treat a patient with constant levels of anti-LT-β-R Abs with reduced ability to signal through the LT-β pathway for semi-prophylactic treatments. Likewise, inhibitory anti-LT-β-R Abs with increased affinity for the LT-β-R may be advantageous for short-term treatments.

Anti-LT-β-R Antibodies As LT-β-R Blocking Agents

Anti-LT-β-R antibodies that act as LT-β-R blocking agents may be selected by testing their ability to inhibit LT-β-R-induced cytotoxicity in tumor cells (Example 5).

Figure 3:
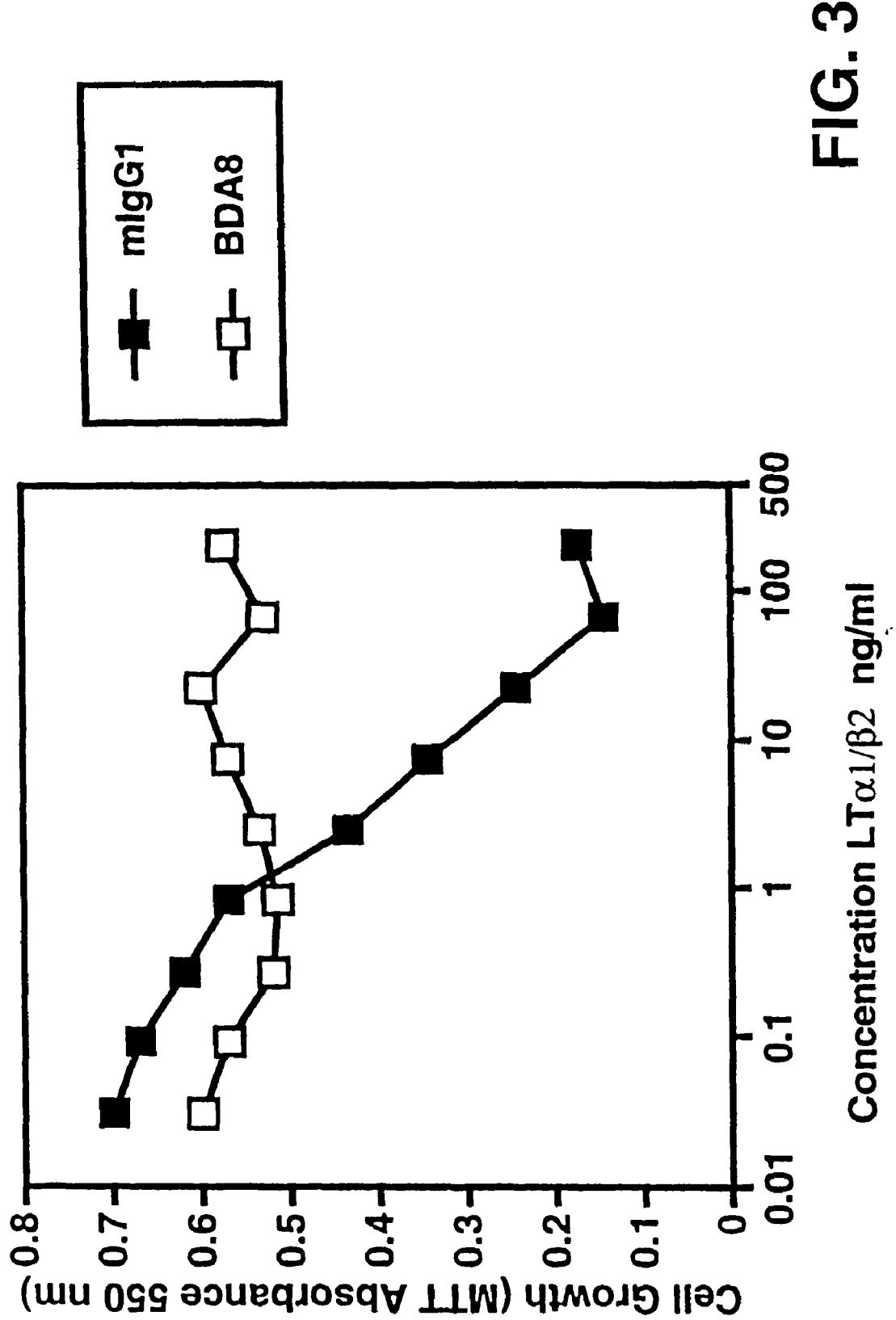
FIG. 3. An antibody directed against human LT-β-R (BDA8 mAb) blocks the interaction between soluble LT ligand and LT-β-R on a human cell surface. The growth of WiDr tumor cells is blocked by a combination of IFN-γ and soluble LT-α1/β2 ligand. The anti-LT-β-R antibody BDA8 blocks the ability of LT-α1/β2 ligand to inhibit the growth of WiDr tumor cells. Solid symbols show cell growth in the presence of IgG1 control mAb (10 μg/ml). Open symbols show the effects of anti-LT-β-R mAb BDA8 (10 μg/ml).

In a preferred embodiment of this invention, compositions and methods comprise the mouse anti-human LT-β-R mAb BDA8. FIG. 3 shows that mAb BDA8 acts as a LT-β-R blocking agent as defined by this invention. WiDr tumor cells stop growing in the presence of IFN-γ and soluble LT-α1/β2 ligand. Control antibodies (IgG1) have no effect on this growth inhibition. In contrast, the anti-LT-β-R mAb BDA8 blocks the ability of soluble LT-α1/β2 ligand to inhibit WiDr cell growth. Thus an antibody directed against human LT-β-R can function as a LT-β-R blocking agent as defined by the present invention.

By testing other antibodies directed against the human LT-β receptor, it is expected that additional anti-LT-β-R antibodies that function as LT-β-R blocking agents in humans can be identified using routine experimentation and the assays described herein.

Source of Anti-Surface LT Ligand Antibodies

Another preferred embodiment of this invention involves compositions and methods which comprise antibodies directed against LT ligand that function as LT-β-R blocking agents. As described above for the anti-LT-β-R Abs, anti-LT ligand antibodies that function as LT-β-R blocking agents can be polyclonal or monoclonal, and can be modified according to routine procedures to modulate their antigen binding properties and their immunogenicity.

The anti-LT antibodies of this invention can be raised against either one of the two LT subunits individually, including soluble, mutant, altered and chimeric forms of the LT subunit. If LT subunits are used as the antigen, preferably they are LT-β subunits. If LT-α subunits are used, it is preferred that the resulting anti-LT-α antibodies bind to surface LT ligand and do not cross-react with secreted LT-α or modulate TNF-R activity (according to the assays described in Example 3).

Alternatively, antibodies directed against a homomeric (LT-β) or a heteromeric (LT-α/β) complex comprising one or more LT subunits can be raised and screened for activity as LT-β-R blocking agents. Preferably, LT-α1/β2 complexes are used as the antigen. As discussed above, it is preferred that the resulting anti-LT-α1/β2 antibodies bind to surface LT ligand without binding to secreted LT-α and without affecting TNF-R activity.

The production of polyclonal anti-human LT-α antibodies is described in applicants' co-pending application (WO 94/13808). Monoclonal anti-LT-α and anti-LT-β antibodies have also been described (Browning et al., J. Immunol., 154, pp. 33–46 (1995)).

Mouse anti-human LT-β mAbs were prepared as described in Example 6. A hybridoma cell line (B9.C9.1) which produces the mouse anti-human LT-β-R mAb β9 was deposited on July 21, 1995 with the American Type Culture Collection (ATCC) (Rockville, Md.) according to the provisions of the Budapest Treaty, and was assigned the ATCC accession number.

Monoclonal hamster anti-mouse LT-α/β antibodies were prepared as described in Example 7. A hybridoma cell line (BB.F6.1) which produces the hamster anti-mouse LT-α/B mAb BB.F6 was deposited on Jul. 21, 1995 with the American Type Culture Collection (ATCC) (Rockville, Md.) according to the provisions of the Budapest Treaty, and was assigned the ATCC accession number.

All restrictions on the availability to the public of the above ATCC deposits will be irrevocably removed upon the granting of a patent on this application.

Anti-LT Ligand Antibodies As LT-β-R Blocking Agents

A fluorescence-activated cell sorting (FACS) assay was developed to screen for antibodies directed against LT subunits and LT complexes that can act as LT-β-R blocking agents (Examples 6 and 7). In this assay, soluble human LT-β-R-Fc fusion protein is added to PMA-activated II-23 cells—which express surface LT complexes (Browning et al., J. Immunol., 154, pp. 33–46 (1995))—in the presence of increasing amounts of the test antibody. An antibody that can inhibit LT-β receptor-ligand interaction by at least 20% is selected as a LT-β-R blocking agent.

Figure 4:
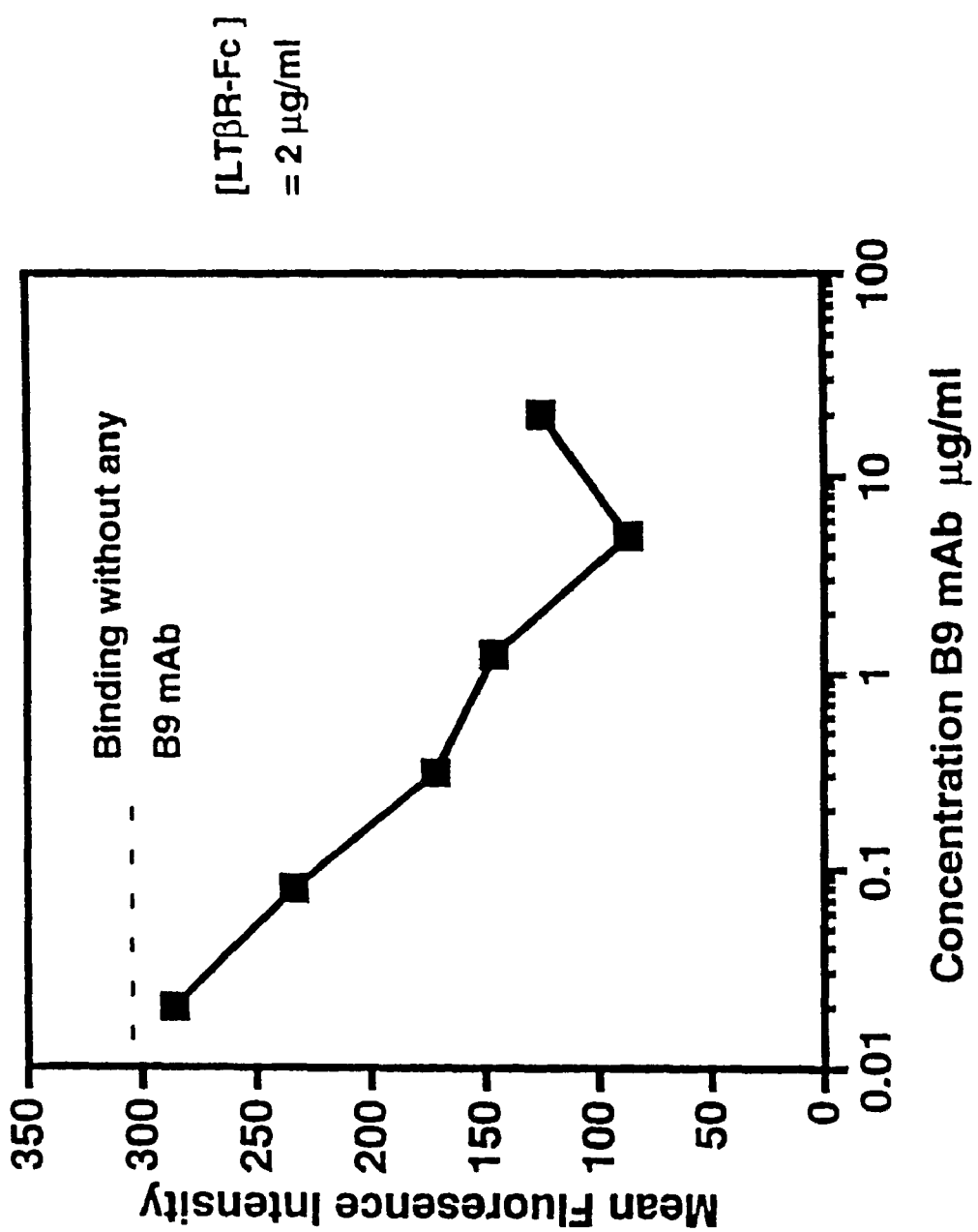
FIG. 4. An antibody directed against human LT-β (B9 mAb) blocks the interaction between cell surface LT-α/β ligand and soluble LT-β receptor (hLT-β-R-Fc; 2 μg/ml). Surface bound LT-β-R-Fc was detected using phycoerythrin-labelled donkey anti-human IgG and FACS analysis. The mean fluorescence intensity of the resultant peak is plotted as channel number. Dotted line shows the mean fluorescence intensity corresponding to the amount of receptor bound in the absence of the B9 mAb.

The results of this assay performed to test the mouse anti-human LT-β mAb B9 are shown in FIG. 4. FIG. 4 shows that anti-LT-β mAb B9 can selectively block the binding of soluble LT-β-R-Fc fusion proteins to surface LT ligands induced on activated cells. These results confirm that antibodies directed against a LT ligand subunit will function as an LT-β-R blocking agent.

The FACS assay described above was also used to test mAbs raised in hamster against a soluble mouse LT-α/β complex (Example 7). The results of this assay performed to test the hamster anti-mouse LT-α/β mAb BB.F6 are shown in Table 2 (Example 7). Table 2 shows that anti-LT-α/β mAb BB.F6 can effectively block the binding of soluble mLT-β-R-Fc fusion proteins (Example 2) to surface LT ligands expressed on a murine T cell hybridoma and is thus a LT-β-R blocking agent according to this invention.

Using a LT-α/β complex rather than a LT subunit as an antigen to immunize an animal may lead to more efficient immunization, or may result in antibodies having higher affinities for surface LT ligand. It is conceivable that by immunizing with the LT-α/β complex, antibodies which recognize amino acid residues on both the LT-α and the LT-β subunits (e.g., residues that form an LT-α/β cleft) can be isolated. By testing antibodies directed against human LT-α/β heteromeric complexes, it is expected that additional anti-LT antibodies that function as LT-β-R blocking agents in humans can be identified using routine experimentation and the assays described herein.

LT-β-R Blocking Agents Inhibit Th1 Cell-Mediated Contact Hypersensitivity in Mouse The LT-β-R blocking agents of this invention can inhibit Th1 cell-mediated immune responses. One such Th1-mediated response is delayed-type hypersensitivity (DTH; Cher and Mosmann, *J. Immunol.*, 138, pp. 3688–94 (1987); see also I. Roitt et al., Immunology, pp. 22.1–22.12, Mosby-Year Book Europe Ltd., 3d ed. (1993) for a general discussion). DTH is evoked when antigen-sensitized Th1 cells secrete cytokines following a secondary contact with the same antigen. The Th1 cytokines attract and activate macrophages that release additional effector molecules which trigger inflammatory reactions.

DTH reactions are classified into three different types: contact hypersensitivity, tuberculin-type hypersensitivity and granulomatous reactions. The three types of hypersensitivity (HS) may be distinguished by the speed and nature of the response to foreign antigen when it is applied directly to or injected beneath the skin of a sensitized subject. The DTH reaction is monitored by measuring the rate and degree to which the skin thickens.

Tuberculin-type HS reactions are skin reactions which occur at the injection site of a foreign antigen from a microorganism to which the subject has been previously exposed (e.g. mycobacterium tuberculosis or M. leprae). This skin reaction, which is maximal between 48 and 72 hours, is frequently used as the basis for diagnostic sensitivity tests to previously-encountered microorganisms (e.g. the tuberculin skin test). As a tuberculin-type lesion develops, it can become a granulomatous reaction if the antigen persists in the tissue.

Granulomatous reactions are clinically the most serious DTH reactions because they can lead to many of the pathological effects associated with Th1 cell-mediated diseases. Granulomatous reactions occur when antigens or immune complexes fail to clear from macrophages and continue to stimulate Th1 cytokine secretion. Chronic inflammation and aggregation of activated macrophages at the site of the stimulus characterize granulomatous reactions.

A core of epithelial cells and macrophages, which can also be surrounded by lymphocytes and fibrotic depositions, form a hardened structure called a granuloma. Sometimes there is extensive cell death in the core of the granuloma (e.g. in tuberculosis-affected lung tissue). Hardening in the target tissue of a granulomatous reaction occurs in about 4 weeks.

Agents which affect the frequency of granuloma formation can be identified using schistosome-infected mice (Amiri et al., *Nature*, 356, pp. 604–607 (1992)). Schistosome worms (blood flukes) can cause a parasitic disease leading to granuloma formation around the schistosome eggs deposited in portal venules of the infected liver. Agents that inhibit this Th1 cell-mediated DTH response may decrease the size of the granuloma, or the frequency or rate of granuloma formation in schistosome-infected mouse livers. Cellular reaction to the schistosome eggs can be assessed by quantitating the number and size of granulomas formed in mice treated with increasing concentrations of a putative LT-β-R blocking agent over time.

Contact hypersensitivity (CHS) is a class of DTH in which skin is the target organ. In CHS, an inflammatory response is caused by locally applying a reactive hapten onto the skin. Allergens generally comprise at least one hapten molecule, which is usually too small to be antigenic on its own. The hapten penetrates the epidermis and reacts with a normal protein under the skin to produce a novel antigenic complex.

Re-exposure of a sensitized subject to the hapten triggers the DTH response. The hapten-carrier protein conjugate, in combination with antigen presenting cells, activates effector mechanisms that trigger the release of cytokines (including IL-2, IL-3, IFN-γ and GM-CSF). The cascade of released cytokines causes CD4+ T cells to proliferate, the expression patterns of various cell surface adhesion A molecules to change, and the attraction of T cells and macrophages to the skin at the site of inflammation.

The cytokine cascade and resulting vasodilation, cellular infiltration and edema of the dermis and epidermis leads to swelling and inflammation of the target tissue, which accounts for the measurable skin thickening in response to DTH reactions.

The degree to which a particular hapten can sensitize an individual depends on a variety of factors. These factors include how well the hapten can penetrate the skin and react with a host carrier protein to form a conjugate. One hapten that sensitizes nearly all individuals is 2,4-dinitrofluorobenzene (DNFB).

The skin CHS response to a hapten such as DNFB is a classic animal model for cell-mediated immunity. Localization of this CHS response to the ear of a sensitized mouse allows easy, accurate and reproducible quantitation of this cell-mediated immune response in vivo by measuring ear thickness. The details of the murine CHS reaction and the histopathology of the DNFB-induced inflammatory response have been reported (Chisholm et al., *Eur. J. Immunol.*, 23, pp. 682–688 (1993)).

The ability of DNFB to induce a contact hypersensitivity response in most individuals can be used to identify agents that reduce or eliminate the inflammatory responses associated with Th1 cell-mediated DTH reactions. A soluble murine LT-β-R-Fc fusion protein effectively inhibits DNFB-induced contact hypersensitivity responses in mice (Example 8).

Mice were initially sensitized by applying DNFB onto the bottom of each hind foot on two consecutive days. Five days after the initial sensitization, a sub-irritant dose of DNFB in carrier solution was applied to the surfaces of the left ear. Carrier solution alone was applied to the right ear as a control.

Increasing concentrations of the LT-β-R blocking agent mLT-β-R-Fc (Example 2) were then injected intravenously into the mice (Example 8). Injections of PBS buffer alone, or of a human IgG fusion protein (LFA3-Fc) served as negative controls, and injection of an anti-VLA4-specific mAb (PS/2 mAb) known to inhibit CHS served as a positive control.

Twenty-four hours after challenge, the thickness of each ear (DNFB-challenged and -unchallenged) was measured. Inhibition of the ear swelling response by the LT-β-R blocking agent was judged by comparison of treated groups with their negative control group.

Figure 5:
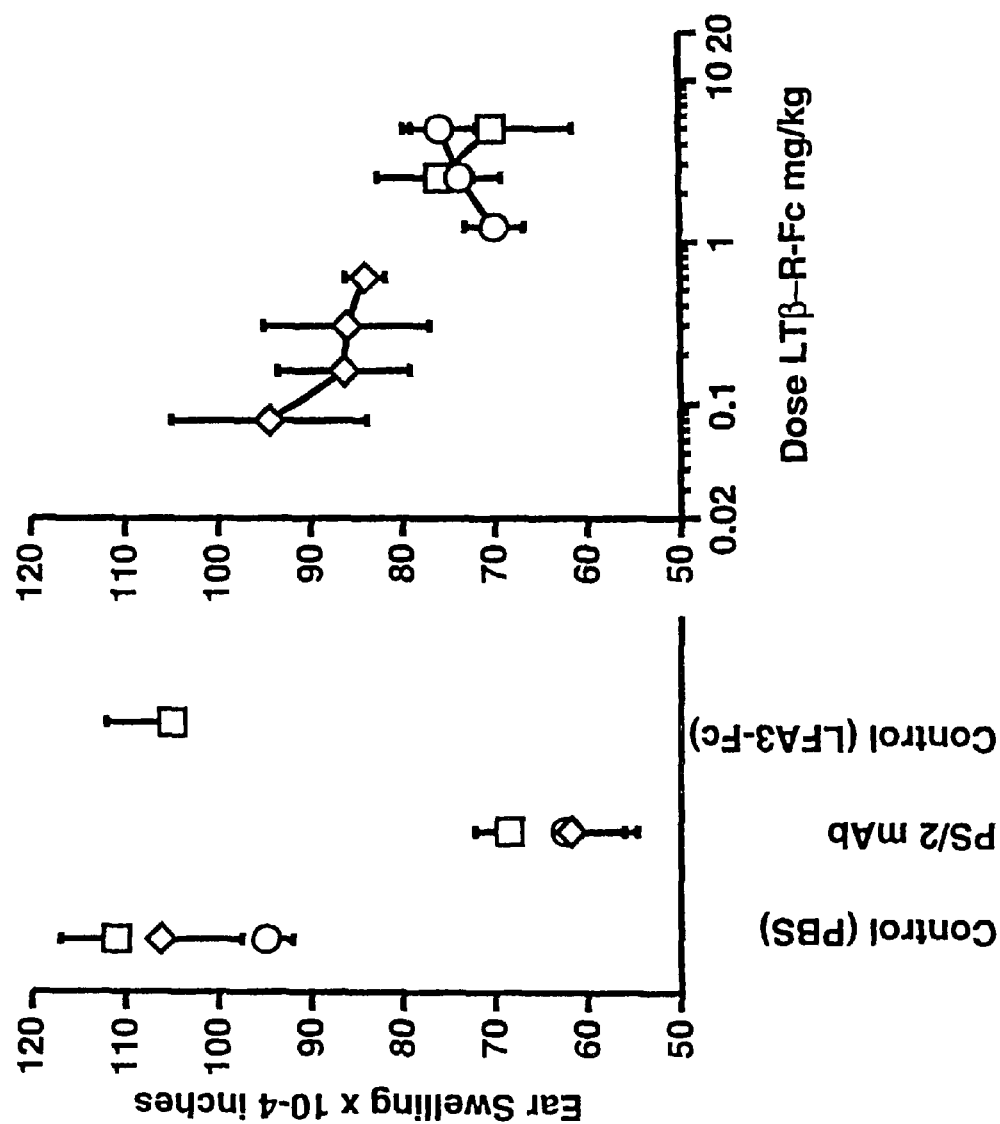
FIG. 5. The effects of a LT-β-R blocking agent (mLT-β-R-Fc) on ear swelling in a mouse contact delayed type hypersensitivity model (DTH). The graph shows the increase in ear thickness measured 24 hours following 0.2% DNFB antigen challenge onto the ears of sensitized mice. Each symbol represents a separate experiment. All experiments utilized 7–8 animals per point except those demarcated with a diamond, which used only 4 animals per point. Mice treated with buffer (PBS) and with 20 mg/kg of a control IgG fusion protein (LFA3-Fc) served as negative controls. Mice treated with 8 mg/kg of an anti-VLA4 mAb (PS/2 mAb), which inhibits contact DTH ear swelling, served as positive controls.

FIG. 5 shows that mLT-β-R-Fc causes a significant reduction in the ear swelling response of DNFB-treated mice compared to uninhibited DNFB-treated control animals (PBS and LFA3-Fc). Soluble LT-β-R can block this CHS reaction as effectively as the inhibitor anti-VLA4-specific mAb (PS/2 mAb), which acts by blocking the influx of T cells into the challenge site (Chisholm et al., *Eur. J. Immunol.*, 23, pp. 682–88 (1993)).

These data show that a soluble LT-β-R fusion protein which acts as a LT-β-R blocking agent in vitro can also effectively inhibit a Th1 cell-mediated immune response when administered to an animal. The LT-β-R blocking agents of this invention identified in vitro can be tested using this ear swelling assay, or other DTH assays such as those described above, to select additional LT-β-R blocking agents that will be useful for reducing the severity of Th1 cell-associated immune responses in vivo.

LT-β-R Blocking Agents Do Not Inhibit a Th2 Cell-Mediated (Humoral) Immunological Response As shown above, the LT-β-R blocking agents of this invention can inhibit a Th1 cell-mediated effector mechanism such as contact delayed type hypersensitivity (FIG. 5). This Th1 cell-mediated response is inhibited without significantly affecting Th2 cell-dependent responses. The differential effect of LT-β-R blocking agents on Th1 cell-mediated immune responses was shown by monitoring a Th2-cell dependent immune response—such as a primary antibody response and isotype switching—in the presence of an LT-β-R blocking agent.

Mice were injected five times over the course of a ten day period with either soluble LT-β-R fusion protein (mLT-β-R-Fc; Example 2) or control IgG fusion protein (LFA3-Fc), or were left untreated. After the second injection, all mice were injected in the base of the tail with 100 µl of complete Freund's adjuvant containing 100 µg of ovalbumin. After 11 days, primary serum anti-ovalbumin-specific antibody titers were analyzed using an ELISA specific for IgG1, IgG2a and IgM isotypes.

Figure 6:
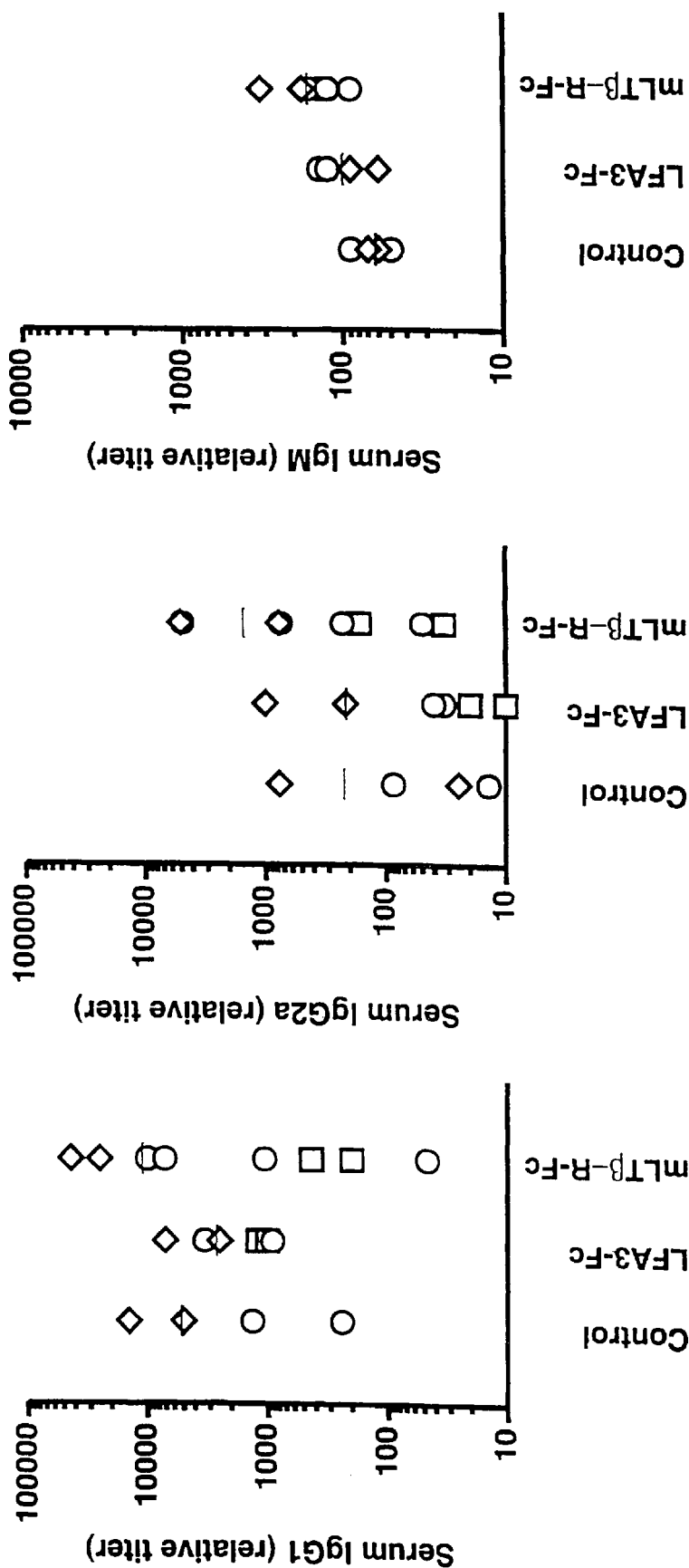
FIG. 6. Treatment with a soluble LT-β-R receptor in vivo does not alter ovalbumin-specific antibody titers following primary immunization of mice with ovalbumin (a Th2 type response). Mice treated with either nothing, 100–200 μg of a LT-β-R fusion protein (mLT-β-R-Fc) or of a control fusion protein (human LFA3-Fc) were immunized with 100 μg ovalbumin in complete Freund's adjuvant at the tail base. Eleven days after the immunization, the mice were sacrificed and the serum anti-ovalbumin antibody titers determined by performing isotype-specific ELISAS. Each point represents the inverse of the serum titer from an individual animal. Data from three separate experiments are indicated with each symbol corresponding to a common experiment.

FIG. 6 shows the effect of the mouse LT-β-R blocking agent mLT-β-R-Fc on serum anti-ovalbumin antibody production in mice immunized with ovalbumin (Example 9). Administering the LT-β-R blocking agent does not significantly affect primary antibody titers following ovalbumin immunization. By comparison, interfering with CD40 ligand-induced CD40 receptor signalling completely blocks the antigen-specific IgG response in mice (Renshaw et al., *J. Exp. Med.*, 180, pp. 1889–1900 (1994)). CD40 is another ligand/receptor pair in the TNF family.

Figure 7:
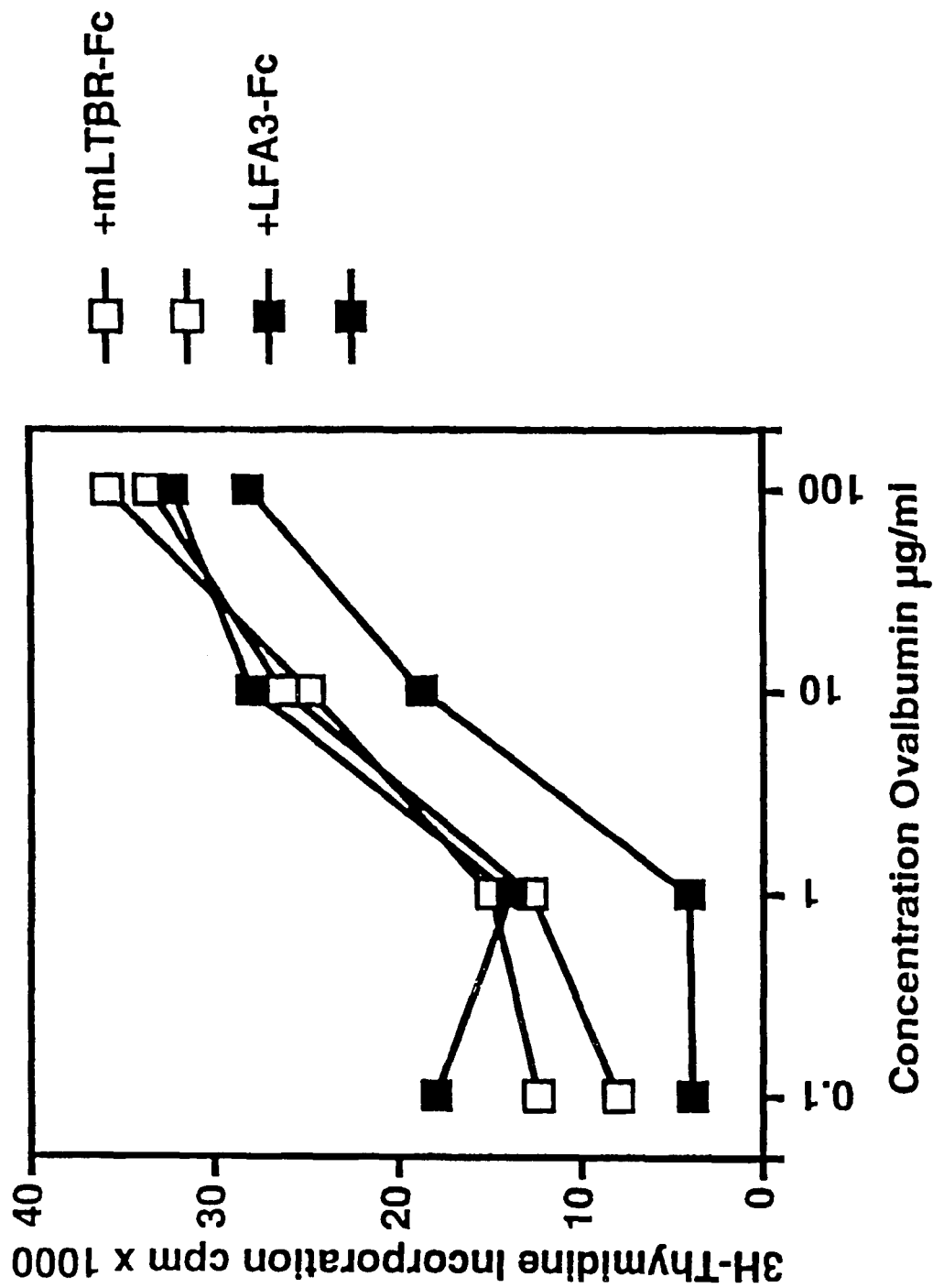
FIG. 7. Treatment with a soluble LT-β receptor in vivo does not affect primed lymphocyte response to restimulation with an antigen (a Th2 type response). Mice treated with either nothing, 200 μg of a LT-β-R fusion protein (mLT-β-R-Fc) or 200 μg of a control fusion protein (human LFA3-Fc) were immunized with 100 μg of ovalbumin in complete Freund's adjuvant at the tail base. Eleven days after the immunization, the mice were sacrificed and lymph node cells were isolated, cultured, and restimulated with ovalbumin antigen. Proliferation of stimulated cells was assessed by measuring $^3$H-thymidine incorporation. Open squares show the levels of $^3$H-thymidine incorporated by ovalbumin-stimulated lymph node cells from mLT-β-R-Fc-treated mice. Solid squares represent $^3$H-thymidine incorporation by lymph node cells from mice treated with a control IgG fusion protein (LFA3-Fc). Each line represents cells from one mouse.

Total immunoglobulin production and maturation is clearly Th2 cell-dependent. However, there is also evidence that the Th1 cytokine IFN-γ participates but is not absolutely required for the switch to the IgG2a subclass (Huang et al., *Science*, 259, pp. 1742–45 (1993)). The LT-β-R blocking agent mLT-β-R-Fc did not inhibit the IgG2a switch in these experiments. It is possible that the LT-β-R blocking agents of this invention do not block this humoral aspect of a Th1 cell-mediated response. In addition, the proliferative responses of lymphocytes from the mLT-β-R-Fc-treated mice were not decreased (Example 10; FIG. 7).

These experiments indicate that a therapy based on administering the LT-β-R blocking agents of this invention will not adversely affect Th2 dependent antibody production functions of an immune response. The normal pattern of antibody response illustrated in FIG. 6 also indicates that an intensive treatment with soluble mLT-β-R-Fc was not toxic to the mice, further indicating the useful therapeutic nature of the compositions and methods set forth in this invention.

T Helper Cell-Mediated Diseases

Many organ-specific autoimmune conditions appear to involve pathological Th1 response. These data have been reviewed (Modlin and Nutman, *Current Opinion in Immunol.*, 5, pp. 511–17 (1993); Romagnani et al., *Ann. Rev. Immunol.*, 12, pp. 227–57 (1994)). These organ-specific autoimmune conditions include: multiple sclerosis, insulin-dependent diabetes, sympathetic ophthalmia, uveitis and psoriasis.

Insulin-dependent diabetes mellitus is an autoimmune disease in which the insulin-producing beta pancreatic cells are destroyed by leukocytes infiltrating into the islets of Langerhans. Diabetes can be rapidly induced in neonatal nonobese diabetic (NOD) mice by transferring activated prediabetic splenocytes. Recently, Th1- or Th2-like cells, otherwise genetically similar, were transferred into neonatal NOD mice. Only the Th1 cells rapidly induced diabetes—and in almost all recipients (Katz et al., *Science*, 268, pp. 1185–88 (1995)). This indicates that the LT-β-R blocking agents of this invention—which can inhibit the effects of a Th1 cell-mediated immune response in vivo—will be useful for treating or preventing insulin-dependent diabetes.

Several systemic autoimmune diseases, including various arthritides, are Th1 cell-associated. Rheumatoid arthritis and Sjorgren's syndrome both appear to involve Th0 and Th1 cells. In contrast, systemic lupus erythematosus (SLE) appears to have an aberrant Th0/Th2 dominated response.

Some chronic inflammatory diseases also appear to have an aberrant Th1 type response, including inflammatory bowel disease, sarcoidosis of the lung and allograft rejection. In general, the exact contribution of auto-antibodies versus specific T cells has not been delineated in these autoimmune diseases. Cellular responses may make major contributions to pathogenicity in those systemic autoimmune diseases currently thought to be primarily antibody driven, e.g. the various arthritides.

The normal immune response to some pathogenic infectious agents also elicits a Th1 response that can become excessive and present itself as a medical problem. Examples of granulomatous reactions (a class of DTH response described above) that lead to severe medical problems include leprosy, granuloma formation in the lungs of tuberculosis patients, sarcoidosis and schistosomiasis (Roitt et al., *Immunology*, pp. 22.5–6 (Mosby-Year Book Europe Ltd., 3d ed. 1993). Psoriasis is also likely to be mediated by Th1 cells.

Cytolytic T cells, i.e. CTLs (CD8 positive T cells) may also subdivide into Th1- and Th2-like populations. Therefore it is possible that much of what is known regarding the Th groups will also apply to CD8+ cells, which are primarily involved in anti-viral and grafted tissue rejection responses.

Treatments Using LT-β-R Blocking Agents

The compositions of this invention will be administered at an effective dose to treat the particular clinical condition addressed. Determination of a preferred pharmaceutical formulation and a therapeutically efficient dose regiment for a given application is well within the skill of the art taking into consideration, for example, the condition and weight of the patient, the extent of desired treatment and the tolerance of the patient for the treatment. Doses of about 1 mg/kg of a soluble LT-β-R are expected to be suitable starting points for optimizing treatment doses.

Determination of a therapeutically effective dose can also be assessed by performing in vitro experiments that measure the concentration of the LT-β-R blocking agent required to coat target cells (LT-β-R or LT ligand-positive cells depending on the blocking agent) for 1 to 14 days. The receptor-ligand binding assays described herein can be used to monitor the cell coating reaction. LT-β-R or LT ligand-positive positive cells can be separated from activated lymphocyte populations using FACS. Based on the results of these in vitro binding assays, a range of suitable LT-β-R blocking agent concentrations can be selected to test in animals according to the assays described herein.

Administration of the soluble LT-β-R molecules, anti-LT ligand and anti-LT-β-R Abs of this invention, alone or in combination, including isolated and purified forms of the antibodies or complexes, their salts or pharmaceutically acceptable derivatives thereof, may be accomplished using any of the conventionally accepted modes of administration of agents which exhibit immunosuppressive activity.

The pharmaceutical compositions used in these therapies may also be in a variety of forms. These include, for example, solid, semi-solid and liquid dosage forms such as tablets, pills, powders, liquid solutions or suspensions, suppositories, and injectable and infusible solutions. The preferred form depends on the intended mode of administration and therapeutic application. Modes of administration may include oral, parenteral, subcutaneous, intravenous, intralesional or topical administration.

The soluble LT-β-R molecules, anti-LT ligand and anti-LT-β-R Abs of this invention may, for example, be placed into sterile, isotonic formulations with or without cofactors which stimulate uptake or stability. The formulation is preferably liquid, or may be lyophilized powder. For example, the soluble LT-β-R molecules, anti-LT ligand and anti-LT-β-R Abs of this invention may be diluted with a formulation buffer comprising 5.0 mg/ml citric acid monohydrate, 2.7 mg/ml trisodium citrate, 41 mg/ml mannitol, 1 mg/ml glycine and 1 mg/ml polysorbate 20. This solution can be lyophilized, stored under refrigeration and reconstituted prior to administration with sterile Water-For-Injection (USP).

The compositions also will preferably include conventional pharmaceutically acceptable carriers well known in the art (see for example Remington's Pharmaceutical Sciences, 16th Edition, 1980, Mac Publishing Company). Such pharmaceutically acceptable carriers may include other medicinal agents, carriers, genetic carriers, adjuvants, excipients, etc., such as human serum albumin or plasma preparations. The compositions are preferably in the form of a unit dose and will usually be administered one or more times a day.

The pharmaceutical compositions of this invention may also be administered using microspheres, liposomes, other microparticulate delivery systems or sustained release formulations placed in, near, or otherwise in communication with affected tissues or the bloodstream. Suitable examples of sustained release carriers include semipermeable polymer matrices in the form of shaped articles such as suppositories or microcapsules. Implantable or microcapsular sustained release matrices include polylactides (U.S. Pat. No. 3,773,319; EP 58,481), copolymers of L-glutamic acid and ethyl-L-glutamate (Sidman et al., Biopolymers, 22, pp. 547–56 (1985)); poly(2-hydroxyethyl-methacrylate) or ethylene vinyl acetate (Langer et al., J. Biomed. Mater. Res., 15, pp. 167–277 (1981); Langer, Chem. Tech., 12, pp. 98–105 (1982)).

Liposomes containing soluble LT-β-R molecules, anti-LT ligand and anti-LT-β-R Abs of this invention, alone or in combination, can be prepared by well-known methods (See, e.g. DE 3,218,121; Epstein et al., Proc. Natl. Acad. Sci. U.S.A., 82, pp. 3688–92 (1985); Hwang et al., Proc. Natl. Acad. Sci. U.S.A., 77, pp. 4030–34 (1980); U.S. Pat. Nos. 4,485,045 and 4,544,545). Ordinarily the liposomes are of the small (about 200–800 Angstroms) unilamellar type in which the lipid content is greater than about 30 mol. % cholesterol. The proportion of cholesterol is selected to control the optimal rate of soluble LT-β-R molecule, anti-LT ligand and anti-LT-β-R Ab release.

The soluble LT-β-R molecules, anti-LT ligand and anti-LT-β-R Abs of this invention may also be attached to liposomes containing other LT-β-R blocking agents, immunosuppressive agents or cytokines to modulate the LT-β-R blocking activity. Attachment of LT-β-R molecules, anti-LT ligand and anti-LT-β-R Abs to liposomes may be accomplished by any known cross-linking agent such as heterobifunctional cross-linking agents that have been widely used to couple toxins or chemotherapeutic agents to antibodies for targeted delivery. Conjugation to liposomes can also be accomplished using the carbohydrate-directed cross-linking reagent 4-(4-maleimidophenyl) butyric acid hydrazide (MPBH) (Duzgunes et al., J. Cell. Biochem. Abst. Suppl. 16E 77 (1992)).

Advantages of Therapeutic Compositions Comprising LT-β-R Blocking Agents

The LT-β-R blocking agents of this invention are capable of selectively inhibiting Th1 and not Th2 cell-dependent immune effector mechanisms. LT-β-R blocking agents will be useful in treating conditions that are exacerbated by the activities of Th1-type cytokines (e.g., IL-2 and IFN-γ). Because Th1 cytokines can inhibit Th2 cell-dependent responses, LT-β-R blocking agents may also indirectly stimulate certain Th2 cell-dependent responses that are normally inhibited by Th1-induced cytokine cascades.

The ability to selectively suppress Th1 (or indirectly stimulate Th2) cell responses will be useful for treating abnormalities in diverse cell-mediated immune responses including various autoimmune and chronic inflammatory conditions, antigen tolerance, and cellular rejection of tissue grafts and organ transplants.

As discussed above, treatment of Th1 cell-based immunological conditions generally employs immunomodulatory and immunosuppressive agents which have pleiotropic effects on a wide variety of cell types and immunological responses. These non-specific immunosuppressive agents are generally required in high and often cytotoxic doses that cause adverse side effects.

The ability to shift the character of an immunological response is supported in the recent study of mouse diabetes discussed above (Katz et al., Science, 268, pp. 1185–88 (1995)), and in an allogeneic transplant model (Sayegh et al., J. Exp. Med., 181, pp. 1869–74 (1995)). In the latter study, a fusion protein that blocks the CD28-B7 T cell costimulatory pathway was shown to induce renal graft tolerance. The tolerance correlated with a decrease in Th1 cytokines and an increase in Th2 cytokines in vivo. These data indicate that the LT-β-R blocking agents of this invention will be useful in suppressing cellular rejection of tissue grafts and organ transplants by inhibiting Th1 cell-mediated cytokine release.

The LT-β-R blocking agents of the compositions and methods of this invention can be modified to obtain a desirable level of LT-β-R signalling depending on the condition, disorder or disease being treated. It is envisioned that the absolute level of LT-β-R signalling can be fine-tuned by manipulating the concentration and the affinities of the LT-β-R blocking agents for their respective molecular targets.

For example, in one embodiment of this invention, compositions comprising soluble LT-β-R molecules are administered to a subject. The soluble LT-β receptor can effectively compete with cell surface LT-β receptors for binding surface LT ligands. The ability to compete with surface LT ligands depends on the relative concentrations of the soluble and the cell surface LT-β-R molecules, and on their relative affinities for ligand binding.

Soluble LT-β-R molecules harboring mutations that increase or decrease the binding affinity of that mutant soluble LT-β-R with surface LT ligand can be made using standard recombinant DNA techniques well known to those of skill in the art. Large numbers of molecules with site-directed or random mutations can be tested for their ability to act as LT-β-R blocking agents using routine experimentation and the techniques described herein.

Similarly, in another embodiment of this invention, antibodies directed against either the LT-β receptor or one or more of the LT ligand subunits function as LT-β-R blocking agents. The ability for these antibodies to block LT-β receptor signalling can be modified by mutation, chemical modification or by other methods that can vary the effective concentration or activity of the antibody delivered to the subject.

The ability to diminish LT-β-R signalling without completely inhibiting it may be important for establishing or maintaining reduced levels of LT-β-R signalling that support normal immune function while inhibiting Th1-cell mediated responses which are exaggerated or abnormal.

Disruption of the LT-α gene in a mouse leads to aberrant peripheral lymphoid organ development (De Togni et al., Science, 264, pp. 703–7 (1994)). Such mice lacked lymph nodes and their spleens lacked the usually clear demarcation between T and B cell-rich regions in the follicles. We believe that this phenotype is associated with loss of surface LT-induced LT-β-R signalling because similar phenotypes have not been observed by modulating TNF-R activity. The ability to selectively or to partially block the LT-β-R pathway may thus be useful in treating abnormal lymphoid organ development associated with mis- or over-expression of signalling by the LT-β-R pathway.

Some Th1-associated reactions are critical components of a number of cell-mediated immune responses (Romagnani, S., Ann. Rev. Immunol., 12, pp. 227–57 (1994)), and absolute inhibition of Th1 cell activity may not be desirable in certain circumstances. For example, a mouse can effectively resist a parasitic infection when a good Th1 response can be mounted. Infectious agents such as Listeria and Toxoplasma also elicit strong Th1-type responses. In humans, mycobacterium tuberculosis responses appear to be Th1-based. Leishmaniasis pathogenicity correlates with responses similar to the Th1 responses characterized in mouse (Reed and Scott, Current Opinion in Immunol., 5, pp. 524–31 (1993)).

The ability to influence the level of Th1 inhibition by blocking LT-β-R signalling may be important in maximizing the beneficial results which can be achieved by treatments with the LT-β-R blocking agents of this invention.

The following are examples which illustrate the soluble LT-β receptors, anti-LT ligand and anti-LT-β-R antibodies of this invention and the methods used to characterize them. These examples should not be construed as limiting: the examples are included for purposes of illustration and the present invention is limited only by the claims.

EXAMPLE 1

Preparation of Soluble Human LT-β Receptors as Immunoglobulin Fc Fusion Proteins The sequence of a human cDNA clone isolated from a library of human 12p transcribed sequences derived from a somatic cell hybrid (Baens et al., Genomics, 16, pp. 214–18 (1993)), was entered into GenBank and was later identified as the sequence which encodes human LT-β-R. The sequence of this full-length human LT-β-R cDNA clone has been available since 1992 as GenBank entry L04270.

The extracellular domain of LT-β-R up to the transmembrane region (FIG. 1) was amplified by PCR from a cDNA clone using primers that incorporated NotI and SalI restriction enzyme sites on the 5' and 3' ends, respectively (Browning et al., J. Immunol., 154, pp. 33–46 (1995)). The amplified product was cut with NotI and SalI, purified and ligated into a NotI-linearized vector pMDR901 along with a SalI-NotI fragment encoding the Fc region of human IgG1. The resultant vector contained the dihydrofolate reductase gene and the LT-β-R-Fc fusion protein driven by separate promoters.

The vector was electroporated into CHO dhfr⁻ cells and methotrexate-resistant clones were isolated as per standard procedures. The LT-β-R-Fc was secreted into the medium and an ELISA assay was used to select for cell lines producing the highest level of the receptor fusion protein. A high-producing cell line was grown to large numbers and the conditioned medium collected. The pure LT-β receptor fusion protein was isolated by Protein A Sepharose Fast Flow affinity chromatography (Pharmacia).

EXAMPLE 2

Preparation of Soluble Murine LT-β Receptors as Immunoglobulin Fc Fusion Proteins A complete cDNA clone of the mLT-β-R was prepared by ligating a 5' NotI/ApaLI and 3' ApaLI/NotI fragments from two partial cDNA isolates into the NotI site of pCDNA3 (InVitrogen, San Diego, Calif.). The sequence of this cDNA clone is accessible as GenBank entry U29173. No coding sequence differences were noted when compared with another sequence entry for mLT-β-R found in GenBank entry L38423.

A soluble mLT-β-R (hIgG1) fusion protein was prepared by PCR amplification of the full length mLT-β-R cDNA clone as a template and the primers 5'AACTGCAGCGGC-CGCCATGCGCCTGCCC 3' and 5'GACTTTGTCGAC-CATTGCTCCTGGCTCTGGGGG 3'. The amplified product was purified and cut with NotI and SalI and ligated with a SalI/NotI human IgG1 Fc fragment into NotI-linearized and phosphatase-treated SAB132 to form JLB 122. For stable expression, the NotI cassette containing the mLT-β-R-Fc fragment was transferred into the NotI site of pMDR901 forming PSH001 and the vector was transfected into CHO cells as described (Browning et al., J. Immunol., 154, pp. 33–46 (1995)). Cell clones secreting mLT-β-R-Fc were identified by ELISA analysis. The purified receptor fusion protein was isolated from CHO cell supernatants by Protein A Sepharose Fast Flow chromatography (Pharmacia).

EXAMPLE 3
Use of Soluble Human LT-β-R-Fc to Block LT-β Receptor-Ligand Interactions Soluble hLT-β-R-Fc was tested for its ability to block LT ligand binding to the LT-β receptor in the tumor cell cytotoxicity assay described above. In this assay, a soluble form of the LT ligand (hLT-α1/β2), which activates LT-β-R signalling, is used to kill human tumor cells. Inhibitors of LT-β-R signalling can reduce LT-β-R-induced tumor cell cytotoxicity.

Soluble LT-α1/β2 ligands comprise truncated or modified LT-β subunits lacking a functional transmembrane domain. Soluble LT-α1/β2 ligands bind to and stimulate LT-β-R signalling as well as surface forms of LT ligand (Browning et al., *J. Immunol.*, 154, pp. 33–46 (1995)).

Serial dilutions of hLT-α1/β2, hTNF or hLT-α were prepared in 0.05 ml in 96 well plates and 5000 trypsinized HT29 cells (ATCC) added in 0.05 ml media containing 80 U/ml (antiviral units) of hu-IFN-γ. After 4 days, mitochondrial reduction of the dye MTT was measured as follows: 10 µl of MTT was added and after 3 hours, the reduced dye dissolved with 0.09 ml of isopropanol with 10 mM HCl, and the O.D. measured at 550 nm. Soluble receptor forms or pure human IgG were added in 10 µl prior to the addition of the cells to give a final concentration of 5 µg/ml.

Table 1 compares the ability of hLT-β-R-Fc and p55-TNF-R-Fc chimeras (with human IgG as a control) to block the inhibitory effects of various soluble TNF and LT ligands on HT29 tumor cell growth.

TABLE I

Ability of LT-β-R and p55-TNF-R Immunoglobulin Fusion Proteins to Block the Inhibitory Effects of Various TNF and LT Ligands on HT29 Growth
Concentration of Cytotoxic Agent
(ng/ml) Resulting in 50% Growth Inhibition
In the Presence of[a]

| Cytotoxic Agent | hu-IgG control | p55-TNF-R-Fc | LT-β-R-Fc |
|---|---|---|---|
| TNF | 0.08 | >10[b] | 0.08 |
| LT-α | 3 | >1000 | 3 |
| LT-α1/β2 | 5 | 5 | >200 |

[a]Each cytotoxic agent was pre-mixed with the Ig fusion proteins for 10 minutes prior to addition to the cells. The final concentration of fusion protein was 5 µg/ml.
[b]Higher concentrations were not tested.

The data in Table 1 indicate that the soluble human LT-β-R fusion protein (hLT-β-R-Fc) can effectively block the interaction between LT ligand (LT-α1/β2) and cell surface LT-β receptors and is thus a LT-β-R blocking agent according to this invention.

As expected, the soluble TNF-R fusion protein (p55-TNF-R-Fc) completely blocked TNF-induced growth inhibition by binding to TNF and preventing its interaction with surface TNF receptors. This soluble TNF receptor had no effect on LT ligand-mediated anti-proliferative effects. In contrast, the LT-β-R-Fc blocked LT ligand-induced cytotoxic effects but not those of TNF or LT-α. Thus soluble human LT-β-R fusion proteins do not interfere with TNF-R activation by TNF and LT-α ligands.

EXAMPLE 4
Use of Soluble Murine LT-β-R-Fc to Block Mouse LT-β Receptor-Ligand Interactions A soluble murine LT-β receptor coupled to a human IgG1 Fc domain (mLT-β-R-Fc; see Example 2) was tested for its ability to block LT-β receptor-ligand interaction in mouse using a cytotoxicity assay on mouse cells (FIG. 2). The cytotoxicity assay was performed on WEHI 164 cells using essentially the same procedure as was used in the HT29 cell assay described in Example 3 (see also Browning and Ribolini, *J. Immunol.*, 143, pp. 1859–67 (1989)).

FIG. 2 shows the effects of mLT-β-R-Fc on ligand-induced LT-β-R signalling in mouse WEHI 164 cells. As this assay indicates, WEHI 164 cells are killed by treating them with LT-α/β ligand at concentrations ranging from about 1 to 100 ng/ml. Soluble mLT-S-R-Fc (10 A/ml) blocks the LT ligand-activated cell death. Adding a soluble mouse p55-TNF-R-Fc fusion protein or IgG control antibodies (each at 10 µ/ml) had little or no effect on blocking cell death.

These data show that the mLT-β-R-Fc fusion protein can effectively compete with surface LT-β-R molecules for LT ligand binding. These data also show that LT-α/β-induced cytotoxicity is LT-β-R-mediated and can be inhibited by soluble mLT-β-R-Fc, which acts as a LT-β-R blocking agent according to the present invention.

EXAMPLE 5
Use of Anti-human LT-β-R Antibodies to Block LT-β Rreceptor-ligand Interactions Mouse monoclonal antibodies (mAbs) directed against the human LT-β receptor were prepared by intraperitoneal immunization of RBF mice repetitively with a CHO cell-derived hLT-β-R-Fc fusion protein attached to Protein A Sepharose beads in the absence of adjuvant. Animals were finally boosted with soluble hLT-β-R-Fc, both i.p. and i.v., spleen cells were fused via classical protocols and hybridoma supernatants were screened by ELISA (Ling et al., *J. Interferon and Cytokine Res.*, 15, pp. 53–59 (1995)). Hybridoma supernatants were screened further for their ability to block binding of activated II-23 hybridoma cells—which express surface LT-α1/β2—to LT-β-R-Fc coated plates in a cell panning assay. Pure mAbs were prepared by Protein A Sepharose purification (Pharmacia) of IgG from culture supernatants.

To determine whether an anti-LT-β receptor mAb could block LT-β-R signalling initiated by the binding of soluble LT, a tumor cell cytotoxicity assay was performed using WiDr human carcinoma cells. In the cytotoxicity assays, serial dilutions of LT-α1/β2 were prepared in 0.05 ml in 96 well plates and 10 µl of a 100 µg/ml solution containing either control mouse IgG1 mAb or the anti-LT-β receptor mAb was added. 5000 trypsinized WiDr cells (ATCC) were then added to each well in 0.05 ml of media containing 50 U/ml (antiviral units) of hu-IFN-γ. After 4 days, mitochondrial reduction of the dye MTT was measured as follows: 10 µl of MTT was added and after 3 hours, the reduced dye dissolved with 0.09 ml of isopropanol with 10 mM HCl, and the O.D. measured at 550 nm. The amount of purple color is proportional to the amount of cell growth.

FIG. 3 shows that the anti-LT-β-R mAb BDA8 acts as a LT-β-R blocking agent according to this invention. Human WiDr carcinoma cells stop growing in the presence of IFN-γ and soluble LT-α1/β2 ligand (from about 0.05 to 50 ng/ml). An IgG1 control antibody (10 µg/ml) has no effect on this growth inhibition. In contrast, the anti-LT-β-R mAb BDA8 (10 µg/ml) restores the ability of WiDr cells to grow in the presence of soluble LT-α1/β2 ligand.

EXAMPLE 6
Use of Anti-human LT-β Antibodies to Block Receptor-ligand Interactions Anti-human LT-β mAbs were prepared by immunizing RBF mice with washed protein A Sepharose-9E10-rLT-β beads containing about 1–2 µg of human recombinant LT-β in CFA, and followed with one boost of the same material in IFA. Eight weeks after the last boost, mice were given i.v. 30 μg of purified soluble rLT-β (acid eluted off the 9E10 resin) and 20 μg of the same soluble material 2 days later. One day after the second i.v. boost, the spleen cells were fused using classical protocols to create mAbs. Hybridoma supernatants were screened directly by ELISA or by FACS staining of PMA-activated II-23 cells. Pure mAbs were prepared by Protein A Sepharose Fast Flow purification of IgG from culture supernatants (Pharmacia).

A FACS assay was used to select antibodies directed against LT-β that can effectively block the binding of soluble LT-α/β ligand to LT-β receptors on the surface of a cell—thus mimicking the interaction between two cells in vivo. In this assay, soluble human LT-β-R-Fc (2 μg/ml) was allowed to bind to surface LT ligand on PMA-activated II-23 cells (Browning et al., *J. Immunol.*, 154, pp. 33–46 (1995)) in the presence of increasing concentrations of the test anti-LT-β mAb (0.02–20 μg/ml). The cells were washed and the bound LT-β-R-Fc was detected by reaction with phycoerythrin-labelled donkey anti-human IgG. The amount of bound fluorescent label was determined by FACS analysis and the mean fluorescence intensity was plotted.

FIG. 4 shows the results of a FACS assay which measured the ability of the anti-LT-β mAb B9 to block LT-β receptor-ligand interaction as described above. This experiment shows that the anti-LT-β mAb B9 (0.02–5 μg/ml) can specifically and effectively compete for cell surface LT ligand binding with soluble LT-β-R fusion protein (2 μg/ml) and thus qualifies as an LT-β-R blocking agent according to this invention.

EXAMPLE 7
Use of Anti-mouse LT-α/β Antibodies to Block Receptor-ligand Interactions Soluble mouse LT-α/β complexes were prepared as described above for the human soluble LT-α/β complexes. The soluble mouse LT-β subunit was made based on sequence information previously described (Lawton et al., *J. Immunol.*, 154, pp. 239–46 (1995)).

Soluble murine LT-α/β complexes were expressed using the baculovirus/insect cell expression system and the LT-α/β complexes were isolated by affinity chromatography using human p55 TNF-R and LT-β-R columns essentially as described above for the expression and purification of human LT-α/β complexes.

Armenian hamsters were immunized with purified soluble murine LT-α/β complex essentially as described in Example 6. Hamster spleen cells were fused to the mouse P3X hybridoma cell line as described (Sanchez-Madrid et al., *Methods of Enzymoloay*, 121, pp. 239–44 (1986)). Hybridomas were grouped as anti-mLT-β or anti-mLT-α on the basis of their binding characteristics to either the LT-α/β complex or to LT-α alone, respectively. Hybridoma cells were expanded and the antibodies purified from the culture supernatant using Protein A affinity chromatography (Pharmacia).

To assess whether hamster anti-mouse LT-α and LT-β mAbs could block LT ligand binding to mLT-β-R, we used TIMI-4 cells (ATCC), a murine T cell line that expresses surface LT ligand following PMA activation for 7 hours. Hamster anti-mLT-α or anti-mLT-β mAbs were preincubated with the cells for 30 minutes at 4° C. and then washed twice. The washed cells were incubated with 1 μg/ml of mLT-β-R-Fc at 4° C. After 30 minutes, cells were washed free of unbound mLT-β-R-Fc and then incubated for 30 minutes with 10 μg/ml of phycoerythrin-labelled donkey anti-human IgG to detect bound mLT-β-R-Fc. The amount of bound fluorescent label was determined by FACS analysis and the mean fluorescence intensity was calculated.

Using this analysis, it was found that the hamster anti-mLT-β mAb could effectively block soluble LT-β receptor binding to T cell surface LT ligand. The results are shown in Table 2.

TABLE 2

Ability of Anti-mouse LT-β Monoclonal Antibody To Inhibit mLT-β-R-Fc Binding To Murine Surface LT Ligand

| Conc. mAb (μg/ml) | Anti-mLT-β (BB.F6) | | Anti-mLT-α (AF.B3) | |
|---|---|---|---|---|
| | MFCI[b] | % Inh[c] | MFCI[b] | % Inh[c] |
| 0[a] | 6 | — | 6 | — |
| 0 | 85 | 0 | 85 | 0 |
| 0.01 | 71 | 18 | 84 | 2 |
| 0.03 | 67 | 23 | 86 | 0 |
| 0.1 | 51 | 44 | 86 | 0 |
| 0.3 | 36 | 62 | 84 | 2 |
| 1.0 | 29 | 71 | 89 | 0 |
| 3.0 | 17 | 86 | 88 | 0 |
| 10.0 | 11 | 94 | 95 | 0 |
| 30.0 | 10 | 95 | 94 | 0 |
| 100.0 | 8 | 98 | 92 | 0 |

[a] no receptor added
[b] Mean Fluorescence Channel No.
[c] Percent Inhibition

EXAMPLE 8
LT-β-R Blocking Agents Inhibit Th1-Mediated Contact Hypersensitivity in Mouse 20 g female Balb/c mice (Jackson Laboratories, Bar Harbor, Me.) were initially sensitized by applying 25 μL of 0.5% 2,4-dinitrofluorobenzene (DNFB) in 4:1 v/v acetone:olive oil onto the bottom of each hind foot. Twenty-four hours after the initial sensitization, we again sensitized each mouse with 25 μl of the same solution. Sensitizations were performed while restraining the unanesthetized mouse. On day 5 (120 hours after the initial sensitization), we anesthetized the mice with 90:10 mg/kg ketamine:xylazine (i.p.) and applied a sub-irritant dose of 10 μl of 0.2% DNFB to the dorsal and ventral surfaces of the left ear. The right ear received a similar application of the 4:1 v/v acetone:olive oil vehicle.

Four hours after challenging the immune response, we administered increasing concentrations of the mLT-β-R-Fc (0.08–5.0 mg/kg; Example 2) to the mice in 0.1 ml of phosphate buffered saline (PBS) by intravenous injection. Injections of PBS buffer alone, or 20 mg/kg of a human IgG fusion protein (LFA3-Fc) (Miller et al., *J. Exp. Med.*, 178, pp. 211–22 (1993)) served as negative controls. Injection of 8 mg/kg of an anti-VLA4-specific mAb (PS/2 mAb; Chisolm et al., *Eur. J. Immunol.*, 23, pp. 682–88 (1993))—which is known to inhibit CHS by blocking the influx of T cells into the challenge site—served as a positive control. Groups of four to eight mice were treated per concentration of antibody.

Twenty four hours after challenge, mice were again anesthetized with ketamine:xylazine and the ear thickness of both ears measured with an engineer's micrometer to an accuracy of $10^{-4}$ inches. The ear swelling response for each mouse was the difference between its control- and DNFB-challenged ear thickness.

Typical uninhibited ear swelling responses were 95–110× $10^{-4}$ inches. Inhibition of the ear swelling response was judged by comparison of treated groups with their negative control group. Statistical significance of the difference among treatment groups was evaluated using one-way analysis of variance followed by computation of the Tukey- Kramer Honestly Significant Difference (JMP, SAS Institute) using p<0.05.

FIG. 5 shows that administering increasing concentrations of mLT-β-R-Fc causes a significant reduction in the ear swelling response of DNFB-treated mice compared to uninhibited DNFB-treated control animals (PBS and LFA3-Fc). Soluble LT-β-R (from about 1–5 mg/kg) can block this contact DTH reaction as effectively as the inhibitor anti-VLA4-specific mAb. The portion of this ear swelling assay which is not inhibited probably results from "nonspecific" granulocyte infiltration.

EXAMPLE 9

Murine LT-β-R-Fc Does not Affect a Primary Immunoglobulin Response to a Nominal Antigen in Mouse Female Balb/c mice, 2–3 months old (Jackson Laboratories, Bar Harbor, Me.), were injected with either 100–200 μg of mLT-β-R-Fc or LFA3-Fc (a control IgG1 fusion protein) five times over the course of a ten day period. Another group of control mice was left untreated.

After the second injection, all mice were injected in the base of the tail with 100 μl of complete Freund's adjuvant containing 100 μg of emulsified ovalbumin. At day 11, the mice were bled and serum prepared. The mice were sacrificed and the draining lymph nodes and spleens collected. Primary serum anti-ovalbumin-specific antibody titers were analyzed using an ELISA specific for each IgG1, IgG2a and IgM isotype.

Microtiter plates were coated with ovalbumin, blocked, and various dilutions of the serum applied. Bound antibody was detected with anti-IgG1, -IgG2a or -IgM-specific reagents. The reciprocal of the dilution required to decrease the binding to 50% of the saturated level was defined as the titer.

FIG. 6 shows that none of the treatments affected the primary antibody titer following ovalbumin immunization. By comparison, interfering with CD40 ligand-induced CD40 receptor signalling completely blocks the antigen-specific IgG response in mice (Renshaw et al., *J. Exp. Med.*, 180, pp. 1889–1900 (1994)). CD40 is another ligand/receptor pair in the TNF family.

These experiments indicate that a therapy based on the inhibition of LT-receptor interactions with its ligand(s) will not affect the antibody production aspects of an immune response. Moreover, the normal antibody response also indicates that an intensive treatment of mice with soluble mLT-β-R-Fc was not toxic, further indicating the useful therapeutic nature of the compositions and methods set forth in this invention.

EXAMPLE 10

Effects of in Vivo mLT-β-R-Fc Treatment on Ex Vivo Proliferation Response of Primed Lymph Node Lymphocytes To examine further the effect of an LT-β-R blocking agent on a Th2 cell-dependent response in vivo, animals were treated with mLT-β-R-Fc and the ability of their lymphocytes to respond to antigen was measured. Mice were immunized with 100 μg of ovalbumin in complete Freund's adjuvant in the tailbase on day 2. Mice were injected with 200 μg/mouse of mLT-β-R-Fc or LFA3-Fc i.p. in 250 μl of PBS on days 1, 2, 4, 7 and 9. On day 11, lymph nodes were isolated, a single cell suspension prepared and cells were resuspended in RPMI 1640 medium with 10% FCS, glutamine and Penicillin/Streptomycin.

A 0.1 ml aliquot of $10^5$ cells was added to each well of a 96-well plate containing 0.1 ml RPMI with increasing concentrations of ovalbumin. The plate was incubated for 3 days at 37° C. and then pulsed for 18 hours with 1 μCi/well $^3$H-thymidine (New England Nuclear). The cells on each plate were harvested onto glass fiber filter paper using a TomTec harvester (TomTec) and the incorporated thymidine determined by liquid scintillation counting using a LKB Wallac Beta Plate Counter (Pharmacia LKB Nuclear, Gaithersburg, Md.).

FIG. 7 shows that extensive in vivo treatment with mLT-β-R-Fc did not affect the subsequent ability of ovalbumin-primed lymph node lymphocytes to proliferate in response to ex vivo restimulation with the ovalbumin antigen. Parallel treatment with LFA3-Fc, another human IgG-Fc fusion protein, serves as a negative control.

What is claimed is:

1. A method for treating or reducing the advancement, severity or effects of a Th1 cell-associated autoimmune disease in an animal comprising the step of administering a pharmaceutical composition which comprises a therapeutically effective amount of a soluble lymphotoxin-β receptor (LT-β-R) fused to one or more heterologous protein domains and a pharmaceutically acceptable carrier.

2. The method according to claim 1, wherein the animal is a mammal.

3. The method according to claim 2, wherein the mammal is a human.

4. The method according to claim 1, wherein the soluble LT-β-R comprises a ligand binding domain that can selectively bind to a surface LT ligand.

5. The method according to claim 4, wherein the heterologous protein domain comprises a human immunoglobulin Fc domain.

6. The method according to any one of claims 1–4 wherein the Th1 cell-associated autoimmune disease is rheumatoid arthritis.

7. The method according to claim 5 wherein the Th1 cell-associated autoimmune disease is rheumatoid arthritis.

8. The method according to any one of claims 1–4 wherein the Th1 cell-associated autoimmune disease is multiple sclerosis.

9. The method according to claim 5 wherein the Th1 cell-associated autoimmune disease is multiple sclerosis.

10. The method according to any one of claims 1–4 wherein the Th1 cell-associated autoimmune disease is diabetes.

11. The method according to claim 5 wherein the Th1 cell-associated autoimmune disease is diabetes.

12. A pharmaceutical composition comprising a therapeutically effective amount of a soluble lymphotoxin-β receptor (LT-β-R) fused to one or more heterologous protein domains and a pharmaceutically acceptable carrier.

13. The composition according to claim 12, wherein the soluble LT-β-R comprises a LT-β-R ligand binding domain that can selectively bind to a surface LT ligand.

14. The composition according to claim 13, wherein the heterologous protein domain comprises a human immunoglobulin Fc domain.

* * * * *

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
      (A) LENGTH: 197 amino acids
      (B) TYPE: amino acid
      (C) STRANDEDNESS: <Unknown>
      (D) TOPOLOGY: linear (ii) MOLECULE TYPE: peptide (xi) SEQUENCE DESCRIPTION: SEQ ID NO: 1:

```
Ser Gln Pro Gln Ala Val Pro Pro Tyr Ala Ser Glu Asn Gln Thr Cys
 1               5                  10                  15

Arg Asp Gln Glu Lys Glu Tyr Tyr Glu Pro Gln His Arg Ile Cys Cys
                20                  25                  30

Ser Arg Cys Pro Pro Gly Thr Tyr Val Ser Ala Lys Cys Ser Arg Ile
```

```
            35                    40                    45

Arg Asp Thr Val Cys Ala Thr Cys Ala Glu Asn Ser Tyr Asn Glu His
    50                  55                  60

Trp Asn Tyr Leu Thr Ile Cys Gln Leu Cys Arg Pro Cys Asp Pro Val
65                  70                  75                  80

Met Gly Leu Glu Glu Ile Ala Pro Cys Thr Ser Lys Arg Lys Thr Gln
                85                  90                  95

Cys Arg Cys Gln Pro Gly Met Phe Cys Ala Ala Trp Ala Leu Glu Cys
            100                 105                 110

Thr His Cys Glu Leu Leu Ser Asp Cys Pro Pro Gly Thr Glu Ala Glu
        115                 120                 125

Leu Lys Asp Glu Val Gly Lys Gly Asn Asn His Cys Val Pro Cys Lys
    130                 135                 140

Ala Gly His Phe Gln Asn Thr Ser Ser Pro Ser Ala Arg Cys Gln Pro
145                 150                 155                 160

His Thr Arg Cys Glu Asn Gln Gly Leu Val Glu Ala Ala Pro Gly Thr
            165                 170                 175

Ala Gln Ser Asp Thr Thr Cys Lys Asn Pro Leu Glu Pro Leu Pro Pro
            180                 185                 190

Glu Met Ser Gly Thr
            195
```